US007319181B2

(12) United States Patent
Vanavichit et al.

(10) Patent No.: US 7,319,181 B2
(45) Date of Patent: Jan. 15, 2008

(54) TRANSGENIC RICE PLANTS WITH REDUCED EXPRESSION OF OS2AP AND ELEVATED LEVELS OF 2-ACETYL-1-PYRROLINE

(75) Inventors: Apichart Vanavichit, Nakornpathom (TH); Somvong Tragoonrung, Pathumthani (TH); Theerayut Toojinda, Samutsakorn (TH); Samart Wanchana, Nakornpathom (TH); Wintai Kamolsukyunyong, Nakornpathom (TH)

(73) Assignee: National Science & Technology Development Agency, Klong Luang, Phathumthani (TH)

( * ) Notice: Subject to any disclaimer, the term of this patent is extended or adjusted under 35 U.S.C. 154(b) by 0 days.

(21) Appl. No.: 11/043,520

(22) Filed: Jan. 25, 2005

(65) Prior Publication Data

US 2006/0168679 A1 Jul. 27, 2006

(51) Int. Cl.
*C12N 15/82* (2006.01)

(52) U.S. Cl. ....................... 800/285; 800/286; 435/468

(58) Field of Classification Search ..................... None
See application file for complete search history.

(56) References Cited

U.S. PATENT DOCUMENTS 5,702,933 A * 12/1997 Klee et al. .................. 800/283
2006/0123505 A1* 6/2006 Kikuchi et al. ............. 800/278

OTHER PUBLICATIONS

Asayama M. *Oryza sativa* (japonica cultivar-group) BADH2 mRNA for betaine aldehyde dehydrogenase, complete cds. (2003) GenBank Accession # AB096083.*

Bradbury LMT, et al. The gene for fragrance in rice. (2005) Plant Biotechnology Journal, vol. 3, pp. 363-370.*

Nomenclature Committee of the INternational Union of Blochemistry and Molecular Biology (NC-IUBMB) "Classification and nomenclature of enzymes by the reactions they catalyse"; World Wide Web.chem.qmul.ac.uk/iubmb/enzymes/rules.html, pp. 1-15.*

Horiguchi G. RNA silencing in plants: a shortcut to functional analysis. (2004) Differentiation, vol. 72, pp. 65-73.*

Elomaa P. Transformation of antisense constructs of the chalcone synthase gene superfamily into *Gerbera hybrida*: differential effect on the expression of family members; (1996) Molecular Breeding, vol. 2, pp. 41-50.*

Lorieux M. et al. Aroma in rice: genetic analysis of a quantitative trait. (1996) Theor Appl Genet., vol. 93, pp. 1145-1151.*

Wanchana et al. Sequence Variation of BADH is Associated with the Synthesis of 2AP, a Ptent Aroma Determination in rice. (2003) Proceedings of the Conference on Rice Biotechnology 2003, Peach, Pattaya, Thailand, pp. 157-160.*

Wanchana et al. Enhancing 2-acetyl-1-pyrroline synthesis in rice leaves by RNAi-mediated suppression of Os2AP converts non-aromatic to aromatic rice (*Oryza sativa L.*) (2004) Proceedings of the 1st International Conference on Rice for the Future, p. 105.*

Colliver SP, Morris P, and Robbins MP. Differential modification of flavonoid and isoflavonoid biosynthesis with an antisense chalcone synthase construct in transgenic *Lotus corniculatus*. (1997) Plant Molecular Biology, vol. 35, pp. 509-522.*

Bradbury, Louis M.T. et al. (2005) "The gene for fragrance in rice" Plant Biotechnology Journal 3: 363-370.

Christopher, Mandy et al. (Aug. 2004) "Marker assisted selection in rice improvement" Rural Industries Research and Development Corporation: 15 pages.

Elsley, Kevin (Nov. 18, 2004) "Fragrant gene found" The Land: 53.

Garland, Stephen and Robert Henry (May 2001) "Application of Molecular Markers to Rice Breeding in Australia" Rural Industries Research and Development Corporation: 21 pages.

Kamolsukyunyong, W. et al. (Jul. 18, 2003) "Isogenic Lines Carrying the 26.7-kb Genomic Region on Chromosome 8 of KDML105 are Characterized as Aromatic Rice," Proceeding of the Conference on Rice Biotechnology, Peach, Pattaya, Thailand, pp. 151-155.

Kamolsukyunyong, Wintai et al. (2003) "Aroma Gene of Thai Hom Mali Rice," Lab Today, 9:66-69.

Nagsuk, Anujaree et al. (2003) "Identification of 2-Acetyl-1-Pyrroline, the Principal Aromatic Rice Flavor Compound, in Fungus Cultures," Proceedings of the 2nd International Conference on Medicinal Mushrooms & International Conference on Biodiversity and Bioactive Compounds, pp. 395-400.

Vanavichit, A. et al. (Aug. 31-Sep. 3, 2004) "Discovering Genes for Rice Grain Aroma," Proceedings of the 1st International Conference on Rice for the Future, Bangkok, Thailand, pp. 71-80.

Wanchana, S. et al. (Jul. 18, 2003) "Sequence Variation in BADH is Associated with Synthesis of 2AP, a Potent Aroma Determination in Rice," Proceedings of the Conference on Rice Biotechnology 2003, Peach, Pattaya, Thailand, pp. 157-160.

Wanchana, Samart et al. (2001) "Physical Mapping of the Region Proximal to Genes Controlling Aroma in Rice," RGJ-Ph.D. Congress II, Chonburi, Thailand, p. 153.

Wanchana, Samart et al. (2003) "Sequence Variation in BADH is Associated with the Synthesis of 2AP, a Potent Aroma Determination in Rice," RGJ-PH.D. Congress IV, Chonburi, Thailand, p. 162.

Wanchana, Samart et al. (2005) "RNAi-Mediated Suppression of Os2AP Converts Non-aromatic to Aromatic Rice," RGJ-PH.D. Congress VI, Chonburi, Thailand, p. 160.

Wanchana, Samart et al. (Aug. 10-11, 2004) "Sequence Variation on BADH Associated with 2-Acetyl-1-Pyrroline, the Potent Aroma Compound in Rice," The 4th National Symposium on Graduate Research, Lotus Hotel Pang Suan Kaew, Chiang Mai, Thailand, p. 105.

(Continued)

*Primary Examiner*—Anne Kubelik
*Assistant Examiner*—Cathy Kingdon Worley
(74) *Attorney, Agent, or Firm*—Morrison & Foerster LLP

(57) ABSTRACT

The aromatic compound 2-acetyl-1-pyrroline-is the major potent flavor component of all aromatic rice. This present invention provides transgenic rice plants in which 2-acetyl-1-pyrroline is synthesized at a level greater than in naturally occurring non-aromatic varieties. The transgenic plants have reduced expression of the Os2AP gene and protein, resulting in an aromatic phenotype.

4 Claims, 17 Drawing Sheets

OTHER PUBLICATIONS

Wanchana, Samart et al. (Aug. 31-Sep. 3, 2004) "Enhancing 2-Acetyl-1-Pyrroline Synthesis in rice Leaves by RNAi-Mediated Suppression of Os2AP Converts Non-aromatic to Aromatic Rice (*Oryza sativa L.*)," Proceedings of the 1st International Conference on Rice for the Future, Bangkok, Thailand, p. 105.

Wanchana, Samart et al. (2005) "A Rapid Construction of a Physical Contig across a 4.5 cM Region for Rice Grain Aroma Facilitates Marker Enrichment for Positional Cloning," ScienceAsia, 31: 299-306.

* cited by examiner

2AP accumulation analysis

L-Glutamic acid GSA P5C L-Proline 2- acetyl-1-Pyrroline

FIGURE 5A

```
Nipponbare   ATGGCCACGGCGATCCCGCAGCGGCAGCTCTTCGTCGCCGGCGAGTGGCGCGCCCCCGCG
THM          ATGGCCACGGCGATCCCGCAGCGGCAGCTCTTCGTCGCCGGCGAGTGGCGCGCCCCCGCG

Nipponbare   CTCGGCCGCCGCCTCCCCGTCGTCAACCCCGCCACCGAGTCCCCCATCGGCGAGATCCCG
THM          CTCGGCCGCCGCCTCCCCGTCGTCAACCCCGCCACCGAGTCCCCCATCGGCGAGATCCCG

Nipponbare   GCGGGCACGGCGGAGGACGTGGACGCGGCGGTGGCGGCGGCGCGGGAGGCGCTAAGAGG
THM          GCGGGCACGGCGGAGGACGTGGACGCGGCGGTGGCGGCGGCGCGGGAGGCGCTAAAAAG

Nipponbare   AACCGGGGCCGCGACTGGGCGCGCGCGCCGGGCGCCGTCCGGGCCAAGTACCTCCGCGCA
THM          AACCCGGGCCGCGACTGGGCGCCCGCGCCGGGCGCCGTCCGGGCCAAGTACATTCGCGCA

Nipponbare   ATCGCGGCCAAGATAATCGAGAGGAAATCTGAGCTGGCTAGACTAGAGACGCTTGATTGT
THM          ATCGCTGACAAAATAATCGAGAGGAAATCTGAGCTGGCTAGACTAGAGACGCTTGATTGT

Nipponbare   GGGAAGCCTCTTGATGAAGCAGCATGGGACATGGACGATGTTGCTGGATGCTTTGAGTAC
THM          GGGAAGCCTCTTGATGAAGCAGCATGGGACATGGACGATGTTGCTGGATGCTTTGAGTAC

Nipponbare   TTTGCAGATCTTGCAGAATCCTTGGACAAAAGGCAAAATGCACCTGTCTCTCTTCCAATG
THM          TTTGCAGATCTTGCAGAATCCTTGGACAAAAGGCAAAATGCACCTGTCTCTCTTCCAATG

Nipponbare   GAAAACTTTAAATGCTATCTTCGGAAAGAGCCTATCGGTGTAGTTGGGTTGATCACACCT
THM          GAAAACTTTAAATGCTATCTTCGGAAAGAGCCTATCGGTGTAGTTGGGTTGATCACACCT

Nipponbare   TGGAACTATCCTCTCCTGATGGCAACATGGAAGGTAGCTCCTGCCCTGGCTGCTGGCTGT
THM          TGGAACTATCCTCTCCTGATGGCAACATGGAAGGTAGCTCCTGCCCTGGCTGCTGGCTGT

Nipponbare   ACAGCTGTACTAAAACCATCTGAATTGGCTTCCGTGACTTGTTTGGAGCTTGCTGATGTG
THM          ACAGCTGTACTAAAACCATCTGAATTGGCTTCCGTGACTTGTTTGGAGCTTGCTGATGTG

Nipponbare   TGTAAAGAGGTTGGTCTTCCTTCAGGTGTGCTAAACATAGTGACTGGATTAGGTTCTGAA
THM          TGTAAAGAGGTTGGTCTTCCTTCAGGTGTGCTAAACATAGTGACTGGATTAGGTTCTGAA

Nipponbare   GCCGGTGCTCCTTTGTCATCACACCCTGGTGTAGACAAGGTTGCATTTACTGGGAGTTAT
THM          GCCGGTGCTCCTTTGTCATCACACCCTGGTGTAGACAAGGTTGCATTTACTGGGAGTTAT

Nipponbare   GAAACTGGTAAAAAGATTATGGCTTCAGCTGCTCCTATGGTTAAGCCTGTTTCACTGGAA
THM          GAAACTGGTAAATA--------TTTCAGCTGCTCCTATGGTTAAGCCTGTTTCACTGGAA

Nipponbare   CTTGGTGGAAAAAGTCCTATAGTGGTGTTTGATGATGTTGATGTTGAAAAAGCTGTTGAG
THM          CTTGGTGGAAAAAGTCCTATAGTGGTGTTTGATGATGTTGATGTTGAAAAAGCTGTTGAG

Nipponbare   TGGACTCTCTTTGGTTGCTTTTGGACCAATGGCCAGATTTGCAGTGCAACATCGCGTCTT
THM          TGGACTCTCTTTGGTTGCTTTTGGACCAATGGCCAGATTTGCAGTGCAACATCGCGTCTT

Nipponbare   ATTCTTCATAAAAAAATCGCTAAAGAATTTCAAGAAAGGATGGTTGCATGGGCCAAAAAT
THM          ATTCTTCATAAAAAAATCGCTAAAGAATTTCAAGAAAGGATGGTTGCATGGGCCAAAAAT

Nipponbare   ATTAAGGTGTCAGATCCACTTGAAGAGGGTTGCAGGCTTGGCCCGTTGTTAGTGAAGGA
THM          ATTAAGGTGTCAGATCCACTTGAAGAGGGTTGCAGGCTTGGCCCGTTGTTAGTGAAGGA

Nipponbare   CAGTATGAGAAGATTAAGCAATTTGTATCTACCGCCAAAAGCCAAGGTGCTACCATTCTG
THM          CAGTATGAGAAGATTAAGCAATTTGTATCTACCGCCAAAAGCCAAGGTGCTACCATTCTG

Nipponbare   ACTGGTGGGGTTAGACCCAAGCATCTGGAGAAAGGTTTCTATATTGAACCCACAATCATT
THM          ACTGGTGGGGTTAGACCCAAGCATCTGGAGAAAGGTTTCTATATTGAACCCACAATCATT

Nipponbare   ACTGATGTCGATACATCAATGCAAATTTGGAGGGAAGAAGTTTTTGGTCCAGTGCTCTGT
THM          ACTGATGTCGATACATCAATGCAAATTTGGAGGGAAGAAGTTTTTGGTCCAGTGCTCTGT

Nipponbare   GTGAAAGAATTTAGCACTGAAGAAGAAGCCATTGAATTGGCCAACGATACTCATTATGGT
THM          GTGAAAGAATTTAGCACTGAAGAAGAAGCCATTGAATTGGCCAACGATACTCATTATGGT

Nipponbare   CTGGCTGGTGCTGTGCTTTCCGGTGACCGCGAGCGATGCCAGAGATTAACTGAGGAGATC
THM          CTGGCTGGTGCTGTGCTTTCCGGTGACCGCGAGCGATGCCAGAGATTAACTGAGGAGATC

Nipponbare   GATGCCGGAATTATCTGGGTGAACTGCTCGCAACCCTGCTTCTGCCAAGCTCCATGGGGC
THM          GATGCCGGAATTATCTGGGTGAACTGCTCGCAACCCTGCTTCTGCCAAGCTCCATGGGGC

Nipponbare   GGGAACAAGCGCAGCGGCTTTGGACGCGAGCTCGGAGAAGGGGGCATTGACAACTACCTA
THM          GGGAACAAGCGCAGCGGCTTTGGACGCGAGCTCGGAGAAGGGGGCATTGACAACTACCTA

Nipponbare   AGCGTCAAGCAAGTGACGGAGTACGCCTCCGATGAGCCGTGGGGATGGTACAAATCCCCT
THM          AGCGTCAAGCAAGTGACGGAGTACGCCTCCGATGAGCCGTGGGGATGGTACAAATCCCCT

Nipponbare   TCCAAGCTGTAA (SEQ ID NO: 5)
THM          TCCAAGCTGTAA (SEQ ID NO: 2)
```

FIGURE 5B 8 bp deletion
in exon 7

```
Nipponbare   TGCATTTACTGGGAGTTATGAAACTGGTAAAAAGATTATGGCTTCAGCTGCTCCTATGGTTAAG (SEQ ID NO: 5)
THM          TGCATTTACTGGGAGTTATGAAACTGGTATATA--------TTTCAGCTGCTCCTATGGTTAAG (SEQ ID NO: 2)
             **************************** * *        *********************

Nipponbare   MATAIPQRQLFVAGEWRAPALGRRLPVVNPATESPIGEIPAGTAEDVDAAVAAAREALKR
THM          MATAIPQRQLFVAGEWRAPALGRRLPVVNPATESPIGEIPAGTAEDVDAAVAAAREALKK

Nipponbare   NKGRDWARAPGAVRAKYLRAIAAKIIERKSELARLETLDCGKPLDEAAWDMDDVAGCFEY
THM          NKGRDWARAPGAVRAKYIRAIAAKIIERKSELARLETLDCGKPLDEAAWDMDDVAGCFEY

Nipponbare   FADLAESLDKRQNAPVSLPMENFKCYLRKEPIGVVGLITPWNYPLLMATWKVAPALAAGC
THM          FADLAESLDKRQNAPVSLPMENFKCYLRKEPIGVVGLITPWNYPLLMATWKVAPALAAGC

Nipponbare   TAVLKPSELASVTCLELADVCKEVGLPSGVLNIVTGLGSEAGAPLSSHPGVDKVAFTGSY
THM          TAVLKPSELASVTCLELADVCKEVGLPSGVLNIVTGLGSEAGAPLSSHPGVDKVAFTGSY

Nipponbare   ETGKKLMASSAPMVKPVSLELGGKSPIVVFDDVDVEKAVEWTLFGCFWTNGQICSATSRL
THM          ETGLYFSCSYG-------------------------------------------------

Nipponbare   ILHKKIAKEFQERMVAWAKNIKVSDPLEEGCRLGPVVSEGQYEKIKQFVSTAKSQGATIL
THM          ------------------------------------------------------------

Nipponbare   TGGVRPKHLEKGFYIEPTIITDVDTSMQIWREEVFGPVLCVKEFSTEEEAIELANDTHYG
THM          ------------------------------------------------------------

Nipponbare   LAGAVLSGDRERCQRLTEEIDAGIIWVNCSQPCFCQAPWGGNKRSGFGRELGEGGIDNYL
THM          ------------------------------------------------------------

Nipponbare   SVKQVTEYASDEPWGWYKSPSKL  (SEQ ID NO: 6)
THM          -----------------------  (SEQ ID NO: 3)
```

FIGURE 8A
**The 8 bp indel PCR-based markers, *Aromarker*, of wild rice**
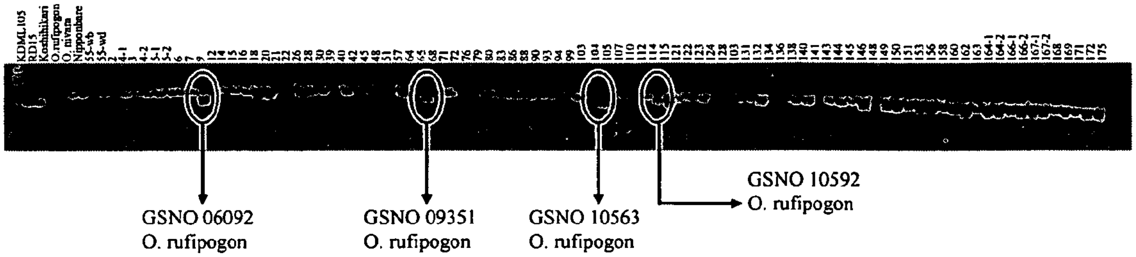
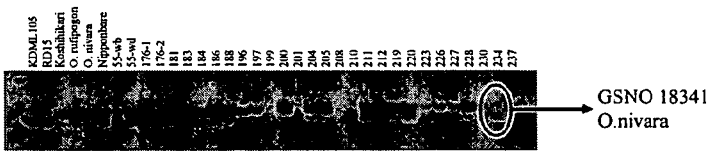
2 - 176_2 *Oryza rufipogon*
181- 237 *Oryza nivara*

FIGURE 9A

```
Thai Hom Mali       TGCATTTACTGGGAGTTATGAAACTGGTATATA-----T---TTCAGCTGCTCCTATGGTTAAG (SEQ ID NO: 2)    aroma (A)
O. Rufipogon 06092  TGCATTTACTGGGAGTTATGAAACTGGTATATA-----T---TTCAGCTGCTCCTATGGTTAAG (SEQ ID NO: 89)   aroma (A)
O. Rufipogon 09351  TGCATTTACTGGGAGTTATGAAACTGGTATATA-----T---TTCAGCTGCTCCTATGGTTAAG (SEQ ID NO: 90)   aroma (A)
O. Rufipogon 10563  TGCATTTACTGGGAGTTATGAAACTGGTATATA-----T---TTCAGCTGCTCCTATGGTTAAG (SEQ ID NO: 91)   aroma (A)
O. rufipogon 07919  TGCATTTACTGGGAGTTATGAAACTGGTAAAAAGATTATGGCTTCAGCTGCTCCTATGGTTAAG (SEQ ID NO: 92)   Non aroma (NA)
O. nivara 18341     TGCATTTACTGGGAGTTATGAAACTGGTATATA-----T---TTCAGCTGCTCCTATGGTTAAG (SEQ ID NO: 93)   aroma (A)
O. nivara 18261     TGCATTTACTGGGAGTTATGAAACTGGTAAAAAGATTATGGCTTCAGCTGCTCCTATGGTTAAG (SEQ ID NO: 94)   Non aroma (NA)
Nipponbare          TGCATTTACTGGGAGTTATGAAACTGGTAAAAAGATTATGGCTTCAGCTGCTCCTATGGTTAAG (SEQ ID NO: 5)    Non aroma (NA)
JHN                 TGCATTTACTGGGAGTTATGAAACTGGTAAAAAGATTATGGCTTCAGCTGCTCCTATGGTTAAG (SEQ ID NO: 95)   Non aroma (NA)
```

TRANSGENIC RICE PLANTS WITH REDUCED EXPRESSION OF OS2AP AND ELEVATED LEVELS OF 2-ACETYL-1-PYRROLINE

FIELD OF THE INVENTION

The present invention relates generally to plant molecular genetics. In particular, it relates to non-naturally occurring plants and fungi that have elevated levels of 2-acetyl-1-pyrroline, methods for making such plants and fungi, and nucleic acids involved in the synthesis of 2-acetyl-1-pyrroline.

BACKGROUND OF THE INVENTION

Grain aroma is the most attractive characteristic of high quality rice increasingly demanded not only by the Asian market but also widely recognized in Europe and all over the world. Cooked rice fragrance is composed of more than one hundred volatile compounds such as hydrocarbons, alcohols, aldehydes, ketones, acids, esters, phenols, pyridines, pyrazines, and other compounds (Yajima et al., 1978; Maga, 1984; Takashi et al., 1980; Paule and Power, 1989). The "popcorn-like" aromatic compound, 2-acetyl-1-pyrroline (2AP), was discovered as the major potent flavor component of all aromatic rice, crust of bread wheat and rye bread (Buttery et al., 1982, 1983). 2-acetyl-1-pyrroline is chiefly responsible for the characteristic fragrance of many aromatic rice varieties (Tanchotikul and Hsieh, 1991). Surprisingly, this rice fragrance has also been isolated and identified from pandan leaves (Buttery et al., 1983), bread flowers (Vallaris Glabra Ktze.) (Wongpornchai et al., 2003), wet millet (Seitz et al., 1993), popcorn (Schieberle, 1991), *Bacillus cereus* (Romanczyk et al., 1995) and fungi (Nagsuk et al., 2004). 2-acetyl-1-pyrroline is present in all parts of the aromatic rice plant (stems, leaves, grains) except roots (Lorieux et al., 1996). While this fragrance is present in aromatic grains, it is not present in all grains.

The aromatic compound 2-acetyl-1-pyrroline has a pyrroline ring similar to the amino acid proline (FIG. 1). The first evidence linking the amino acid proline as the precursor synthesizing 2-acetyl-1-pyrroline was found in experiments in cell and callus culture (Suprasanna et al., 1998; Suprasanna et al., 2002). That conclusion was supported by experiments using isotopic labeling showing that the precursor of the grain 2-acetyl-1-pyrroline is most likely the amino acid proline in Thai Hom Mali (THM) Rice (Yoshihashi et al., 2002) and probably other aromatic rice. However, the exact biosynthetic pathway of 2-acetyl-1-pyrroline is yet to be elucidated. Thus, there is a need to identify genes involved in 2-acetyl-1-pyrroline synthesis and provide a method to increase 2-acetyl-1-pyrroline levels in plants and fungi to increase aroma.

SUMMARY OF THE INVENTION

The present invention meets these needs by providing non-naturally occurring plants and fungi in which the compound 2-acetyl-1-pyrroline is produced at an elevated level compared to control plants and fungi. Control plants and fungi refer to plants and fungi of a similar or related genotype that have lower levels of the compound 2-acetyl-1-pyrroline. Such control plants can be non-naturally occurring. The present invention further provides methods for screening for and creating such non-naturally occurring plants and fungi, and seeds produced from said plants.

The exact biosynthetic pathway of the compound 2-acetyl-1-pyrroline is not known, but it is a derivative of proline. It was hypothesized that proline can be converted either to 2-acetyl-1-pyrroline or to glutamic acid, so inhibition of the glutamic acid synthesis pathway will increase the availability of proline (or intermediates) for 2-acetyl-1-pyrroline synthesis (FIG. 4A). A gene encoding a protein controlling aroma in rice, named Os2AP was identified as a member of the aldehyde dehydrogenase family that may play a key role in the conversion of proline to glutamic acid. All aromatic rice varieties tested have an eight nucleotide deletion in this gene. The deletion creates a premature stop codon that leads to nonsense mediated degradation against its own mRNA, leading to a loss-of-function phenotype. RNA interference (RNAi) studies showed that disruption of transcription of the Os2AP gene led to elevated levels of 2-acetyl-1-pyrroline in plants, along with increased aroma.

The present invention provides non-naturally occurring plants and fungi with an elevated level of 2-acetyl-1-pyrroline created by inhibiting the expression of the Os2AP gene reducing the mRNA levels of the Os2AP gene, and/or reducing the activity of the Os2AP protein. The level of Os2AP protein can be decreased by 25 percent, 50 percent, or 100 percent compared to a control plant. The inhibition of expression of the Os2AP gene or reduction of mRNA levels of the Os2AP gene can be accomplished by: a) expression of the Os2AP gene or a fragment thereof in the antisense orientation; b) cloning part of the gene into an RNA interference construct and expression of this construct in transgenic plants; or c) mutagenesis by various methods (including Targeting Induced Local Lesions IN Genomes (TILLING) and tDNA insertion mutagenesis) followed by screening by PCR or other methods for an aromatic variant.

The present invention further provides a transgenic rice plant having an elevated level of the compound 2-acetyl-1-pyrroline compared to its level in a control non-transgenic rice plant wherein the level of the compound is increased in the transgenic plant by reducing the mRNA or protein levels encoded by the Os2AP gene in the transgenic plant compared to the mRNA or protein levels encoded by the Os2AP gene in the control non-transgenic plant. In one format, the MRNA and protein levels are reduced by RNA interference or by antisense. The invention is further directed to transgenic rice seed produced from the rice of the invention.

Although the examples to follow describe experiments performed in rice, the invention relates to other plants and fungi, including but not limited to wheat, barley, rye, coconut, sorghum, and oats.

The present invention further provides an isolated nucleic acid encoding the Os2AP gene, where said nucleic acid includes a nucleic acid which hybridizes to the nucleic acid sequence depicted in SEQ ID NO: 1, SEQ ID NO: 2, SEQ ID NO: 4 or SEQ ID NO: 5 or its complement under hybridization conditions that include at least one wash in 0.1×SSC and 0.1% SDS at 60-65° C. for thirty minutes, a nucleic acid which is at least 70% identical, 80% identical, 90% identical, 95% identical, or greater than 95% identical to the sequence depicted in SEQ ID NO: 1, SEQ ID NO: 2, SEQ ID NO: 4 or SEQ ID NO: 5, and a nucleic acid that encodes a polypeptide that is at least 70%, at least 80%, at least 90%, at least 95%, or greater than 95% identical to the amino acid sequence depicted in SEQ ID NO: 3 or SEQ ID NO: 6.

The amount of 2-acetyl-1-pyrroline in rice can vary depending on harvest conditions and soil type. A non-aromatic variety, Nipponbare, has 2-acetyl-1-pyrroline levels in the range of 0 to 0.1 ppm (parts per million). In contrast an aromatic rice variety, Thai Hom Mali, has an amount of 2-acetyl-1-pyrroline in the range of 1 to 2.5 ppm. Example 2 details an RNA interference experiment against the rice Os2AP gene, which increased the 2-acetyl-1-pyrroline levels in Nipponbare rice up to 2.5 ppm. The present invention thus provides methods for increasing the level of fragrance in a non-aromatic plant to aromatic levels.

The invention further provides recombinant constructs and expression vectors containing the nucleic acids of the invention, where the nucleic acid can be operably linked to a promoter. One useful promoter is a cauliflower mosaic virus (CaMV) promoter, which confers high levels of expression in most plant tissues.

The invention further provides host cells that contain the nucleic acids, constructs, and expression vectors of the invention.

The invention also provides methods for screening plants and nucleic acids for a mutation in an Os2AP gene leading to a decrease in Os2AP protein expression or activity and a consequent increase in aroma resulting from increased production of the 2-acetyl-1-pyrroline compound. One specific mutation is an eight nucleotide deletion associated with an aromatic phenotype in the rice Os2AP gene. Screening for this and other mutations can be done by a variety of methods, such as PCR, sequencing, hybridization, or microarray experiments. Another option is to look for the reduction of Os2AP protein levels or a change in structure or activity of the Os2AP protein. This could be done, for example, by using an antibody which binds to the active Os2AP protein, or by an assay for Os2AP protein activity.

The sequences described herein can be used as probes or primers in nucleic acid hybridization experiments. Nucleic acid segments that include at least a 14 nucleotide long contiguous sequence that has the same sequence as, or is complementary to, a 14 nucleotide long contiguous DNA segment of the nucleotide sequence depicted in SEQ ID NO: 1, SEQ ID NO: 2, SEQ ID NO: 4 or SEQ ID NO: 5 can be used.

Longer contiguous identical or complementary sequences, e.g., those of about 20, 30, 40, 50, 100, 200, 500, 1,000, 2,000, 5,000, 10,000 etc. (including all intermediate lengths and up to and including full-length sequences will also be of use in certain embodiments.

The ability of such nucleic acid probes to specifically hybridize to Os2AP gene sequences will enable them to be of use in detecting the presence of complementary sequences in a given sample.

However, other uses are envisioned, including the use of the sequence information for the preparation of mutant species primers, or primers for use in preparing other genetic constructions.

Figure 2:
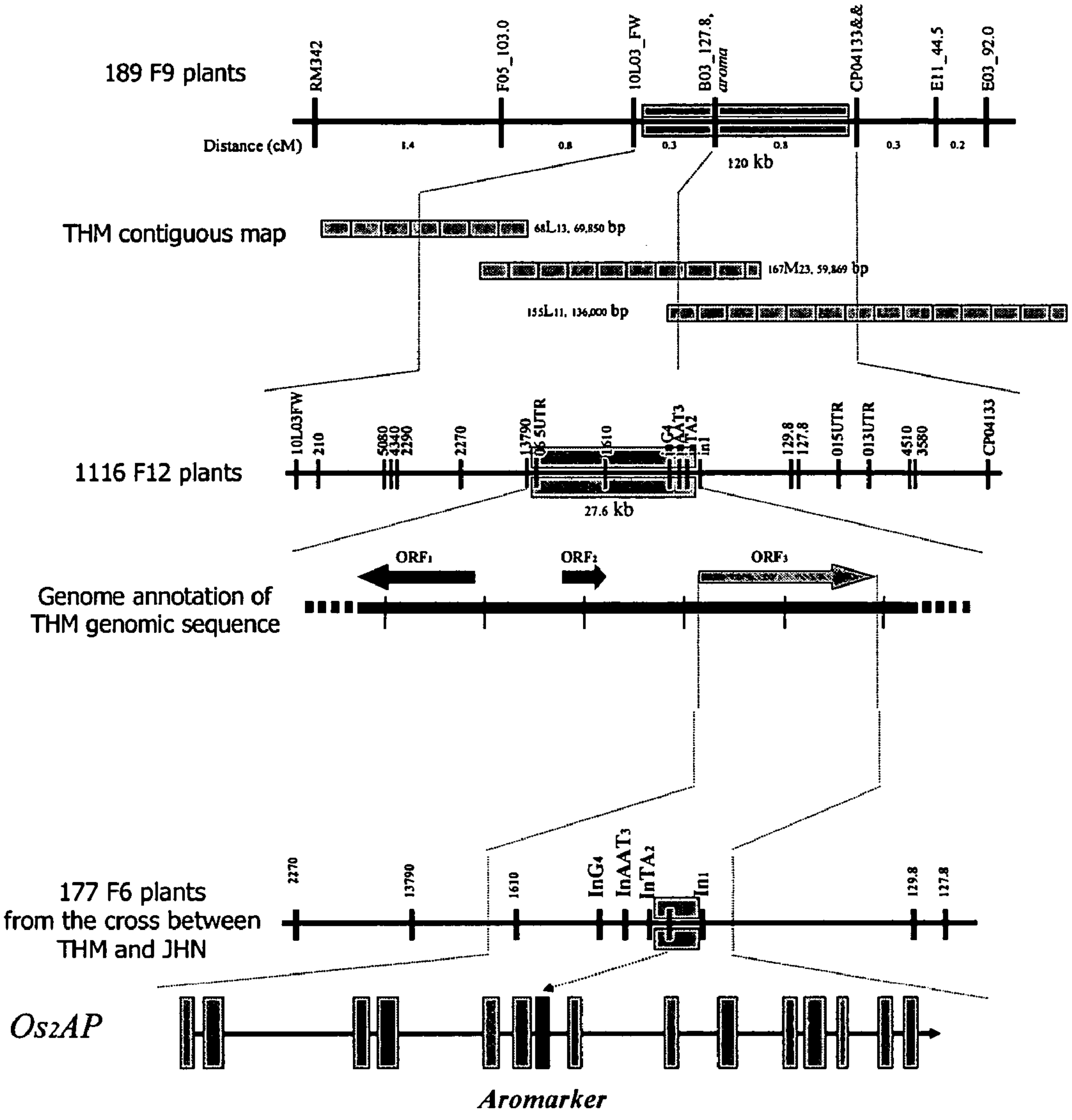
FIG. 2 depicts fine-scale mapping of the aroma gene in rice using 186 F9 plants derived from a single F6 plant segregating for grain aroma and the construction of a physical map encompassing the gene for grain aroma.

The first part of FIG. 2 shows the graphical genotypes of eight F11 plants from the single F6 plant. The second part shows ultrascale mapping using 1116 F12 plants derived from a single F6 plant to narrow down the critical region to 27 kb in a single BAC. The third part shows the annotation of genomic sequence from KDML105 which revealed three open-reading frames. The fourth part shows that using 177 F6 plants from the cross between KDML105 and JHN identified three double recombinants within exon 7 of the unknown protein gene that significantly affects grain aroma and 2-acetyl-1-pyrroline contents. The unknown protein gene was named Os2AP. "Aromarker" is the PCR-based marker defining the 8 base pair deletion and 3 SNPs (single nucleotide polymorphisms) specific to grain aroma.

Figure 3A:
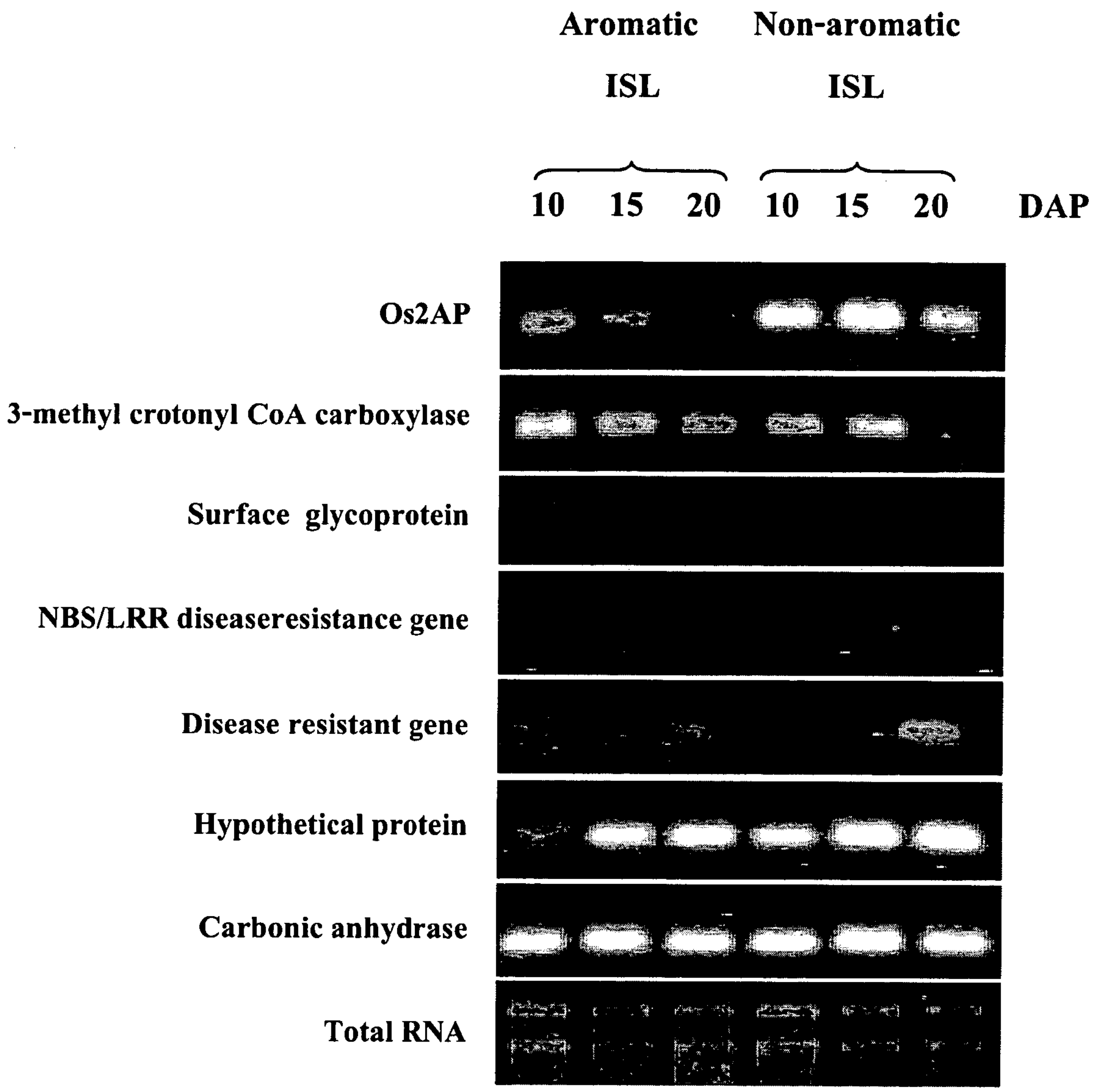

FIG. 3A depicts expression of seven candidate genes using RT-PCR from total RNA isolated from 10, 15 and 20 days after pollination between aromatic and non-aromatic isogenic lines.

Figure 3B:
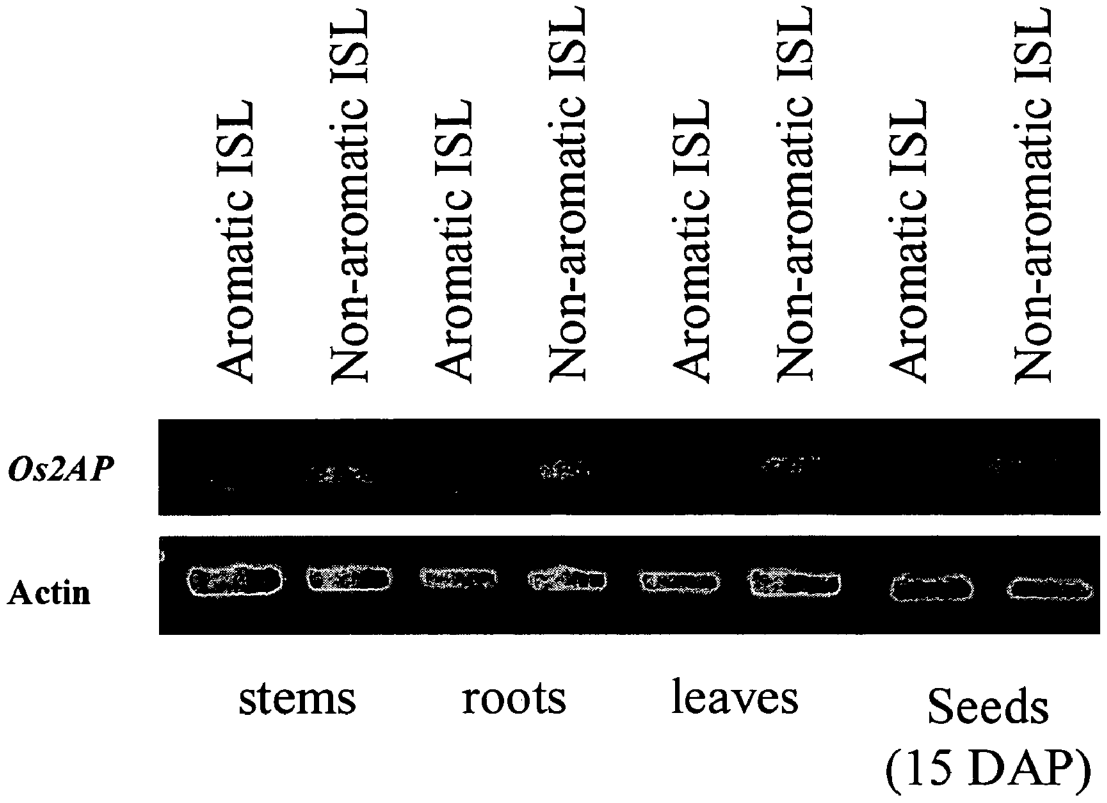

FIG. 3B depicts differential expression of Os2AP transcripts in leaves, stems and roots from total RNA isolated 15 days after pollination between aromatic and non-aromatic isogenic lines.

Figure 3C:
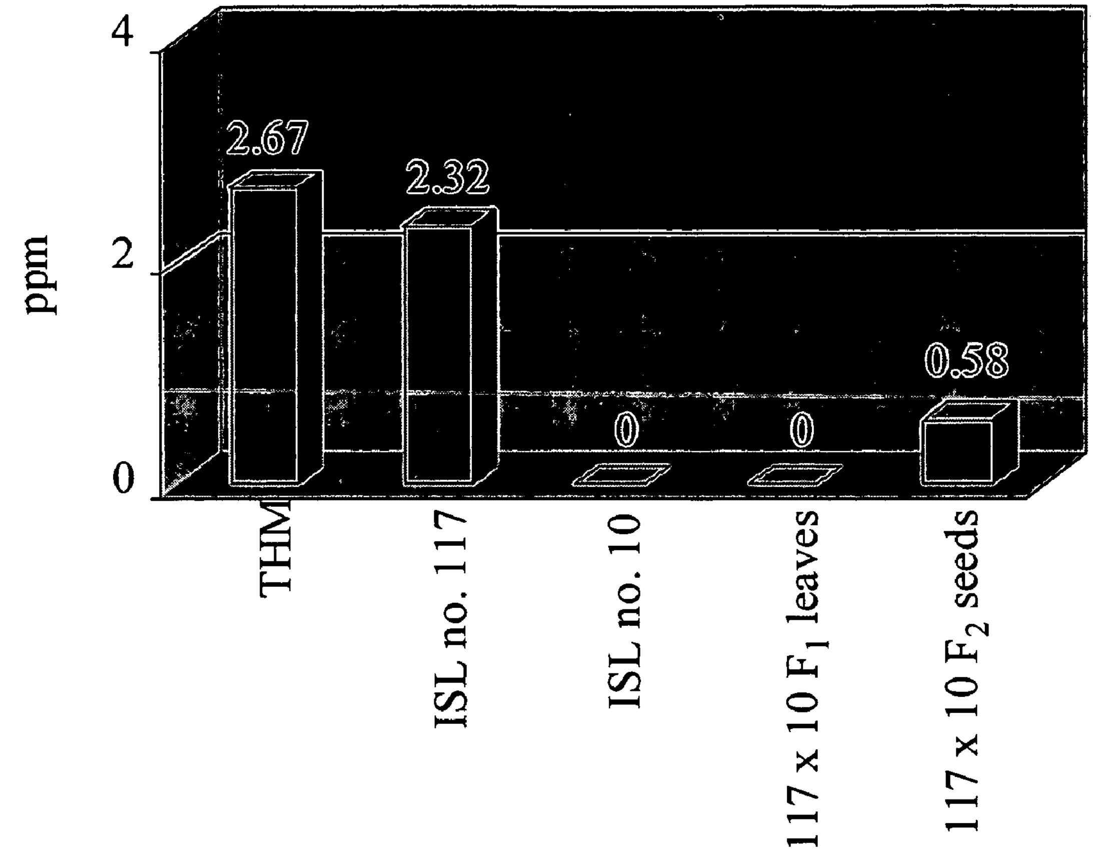

FIG. 3C depicts analysis of 2-acetyl-1-pyrroline levels in grains of THM (KDML105), aromatic isogenic line 117, non-aromatic isogenic line 10, and their F2 (ISL117×ISL10). In F1, analysis of 2-acetyl-1-pyrroline levels was conducted in leaves.

Figure 3D:
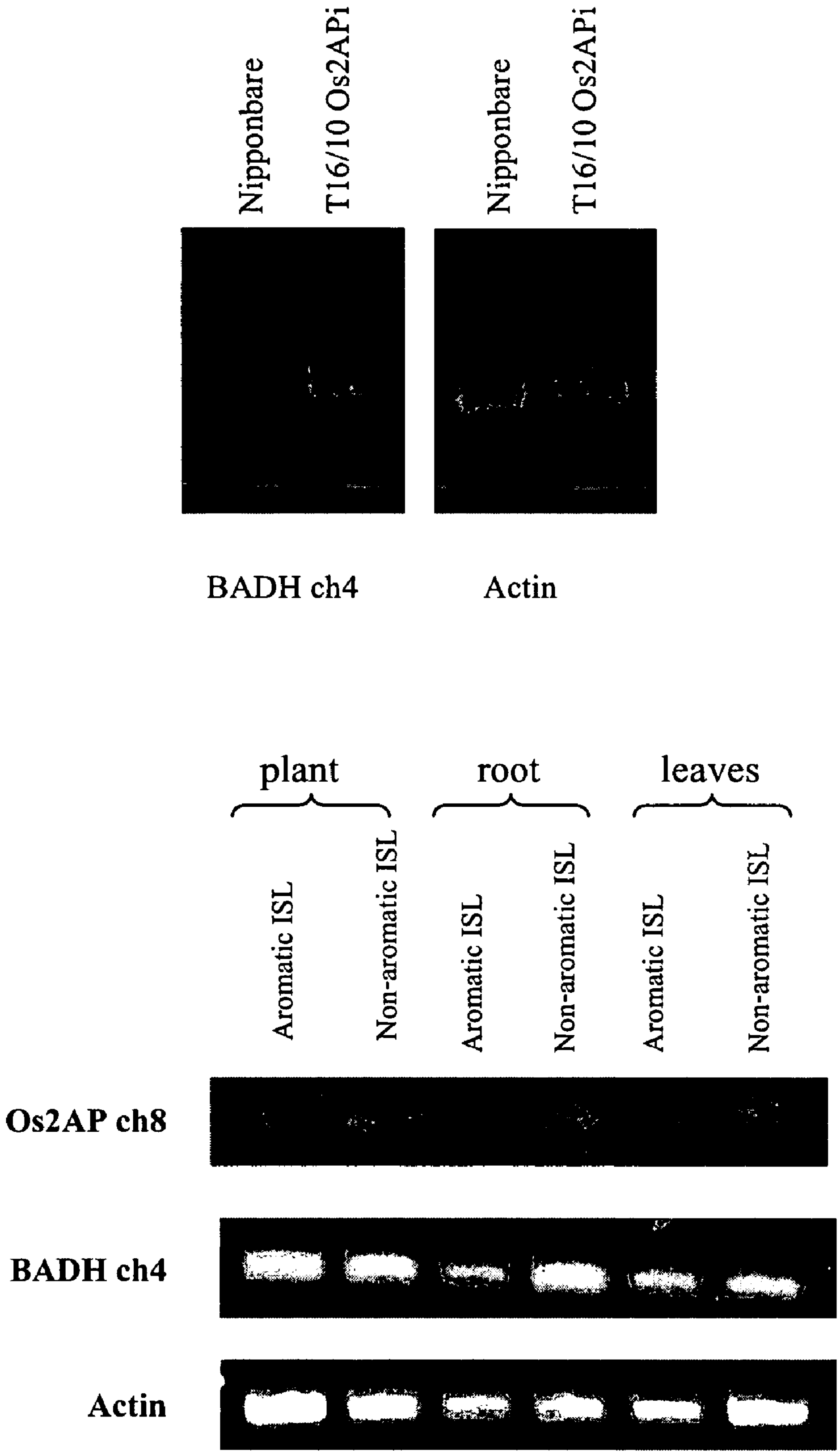

FIG. 3D, upper panel, depicts expression of the BADH gene from chromosome 4 and actin in transgenic Nipponbare carrying Os2AP RNAi construct. FIG. 3D, lower panel, depicts the Os2AP gene on chromosome 8, not the BADH gene on chromosome 4, showing differential expression in aromatic and non-aromatic isogenic lines of rice.

Figure 4A:
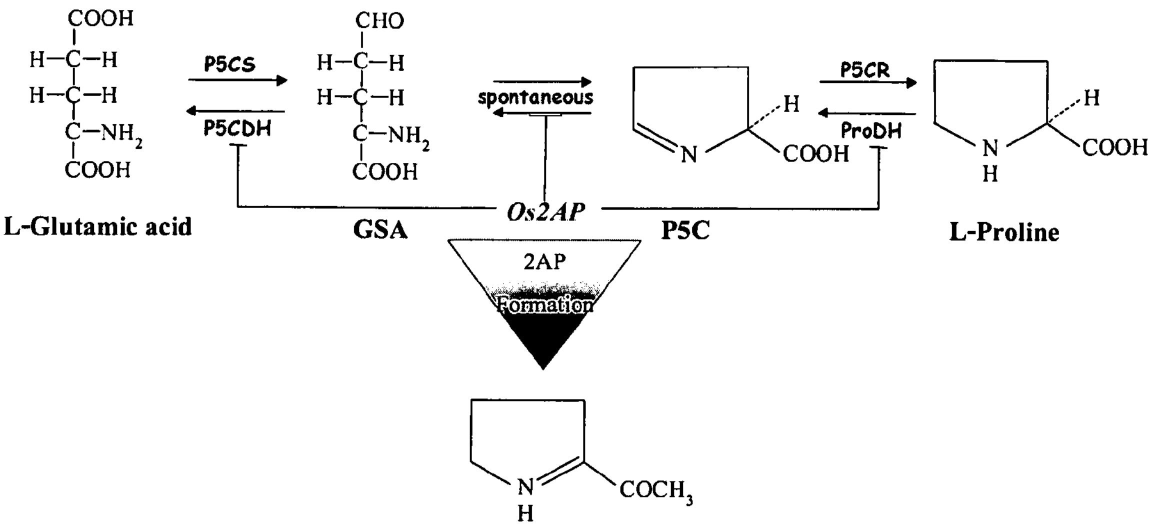

FIG. 4A shows the metabolic pathway between proline and glutamic acid. L-proline can be synthesized from glutamic acid using enzyme P5C synthase (P5CS) and P5C reductase (P5CR), and glutamic acid can be synthesized from proline using proline dehydrognase (PropH), and P5C dehydrogenase (P5CDH). The proposed metabolic shift was mediated by nonsense mutation of the Os2AP gene.

Figure 4B:
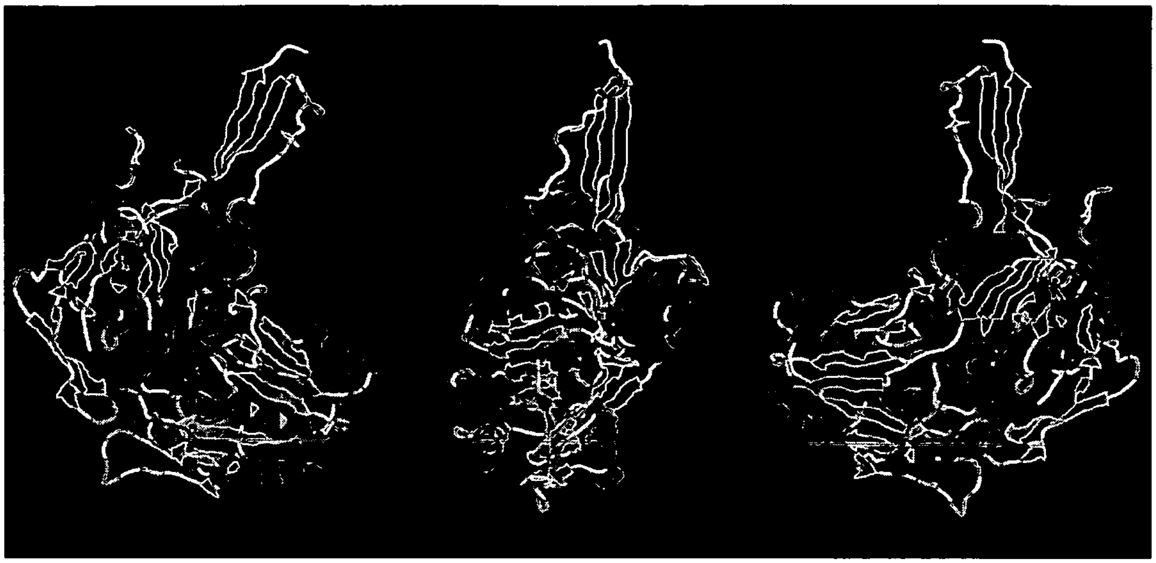

FIG. 4B shows the predicted protein structure of the Os2AP enzyme created by using RASMOL, a program available through the website of the Microbiology Department of the University of Massachusetts, Amherst, USA (new version is Protein Explorer).

FIG. 5A shows the genomic sequence comparison of Os2AP genes from KDML105 (aromatic) and Nipponbare (non-aromatic).

FIG. 5B depicts a DNA alignment showing an eight base pair deletion in Os2AP in an aromatic strain, Thai Hom Mali (THM) as compared to Nipponbare, a non-aromatic strain, and the amino acid sequence comparison between the two strains. The nucleotide sequences in the alignment include nucleotides 701 to 765 from SEQ ID NO: 5 and nucleotides 701 to 757 form SEQ ID NO: 2.

Figure 6:
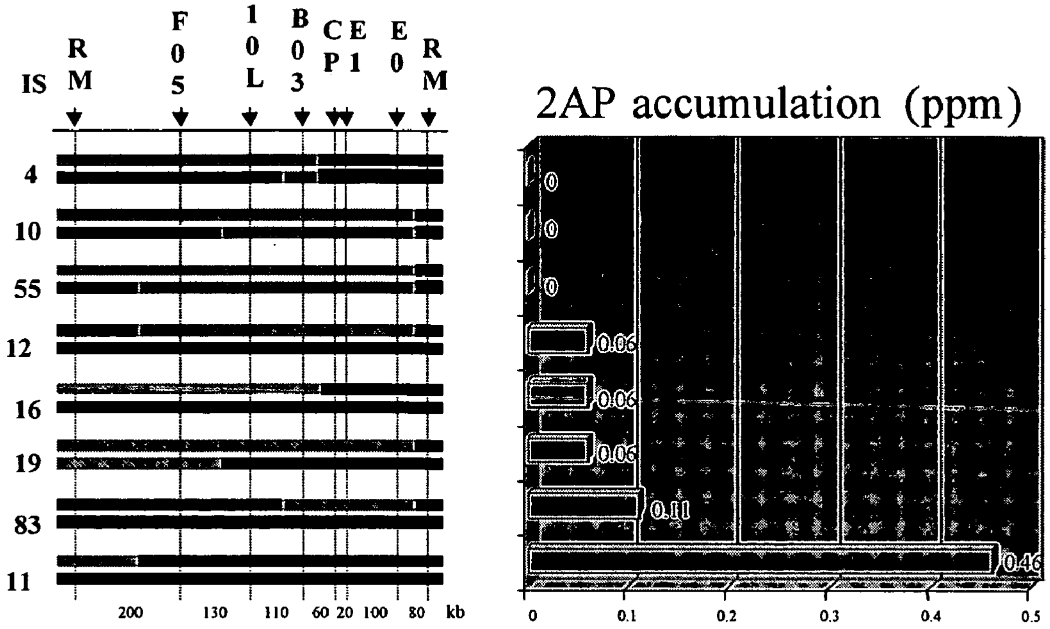

FIG. 6 depicts graphical genotypes of eight F11 plants from the single F6 plant and the analysis of 2-acetyl-1-pyrroline levels from the rice grains.

Figure 7A:
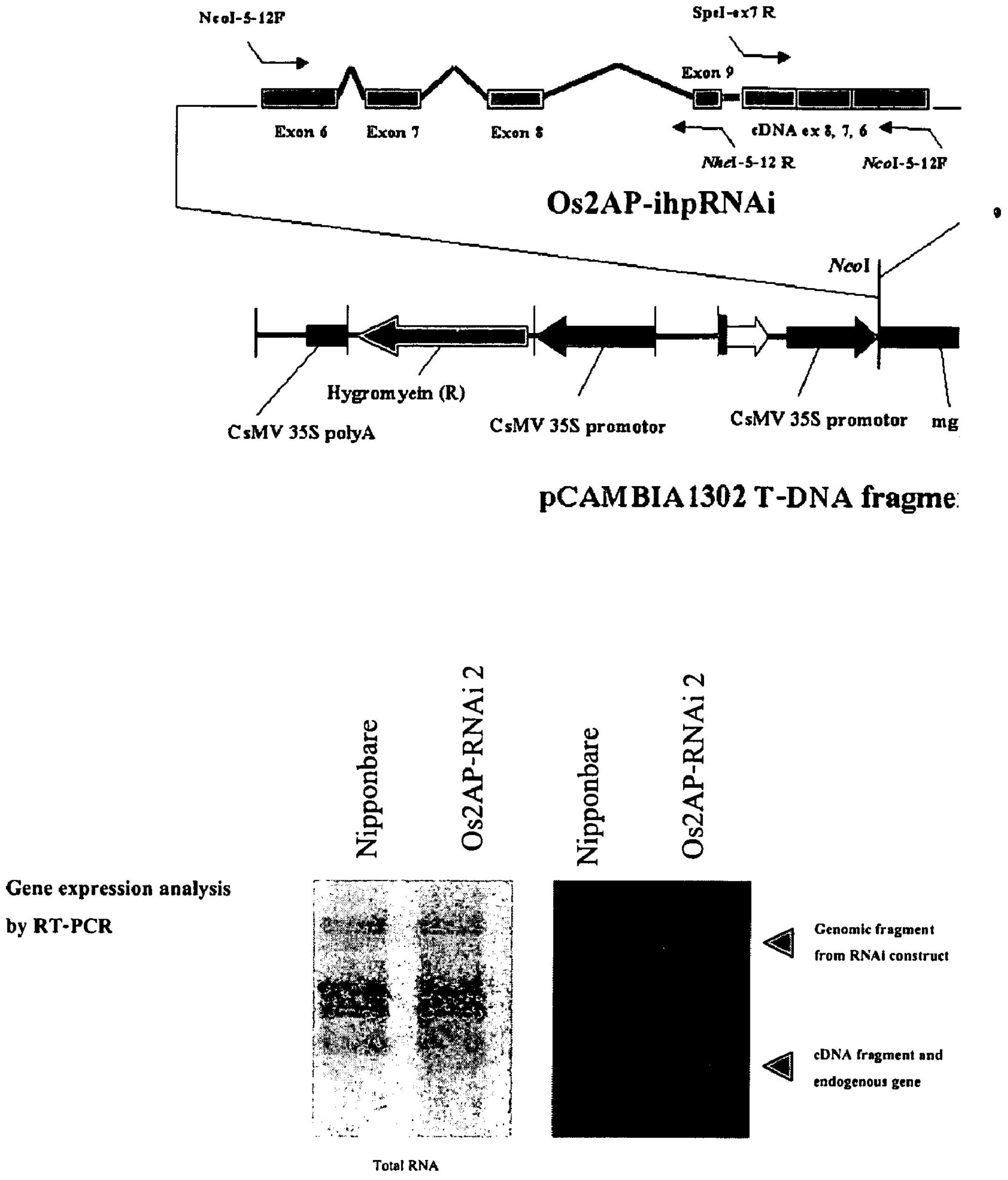

FIG. 7A depicts an RNA interference construct and vector for transformation. The lower panel shows confirmation of expression of the construct.

Figure 7B:
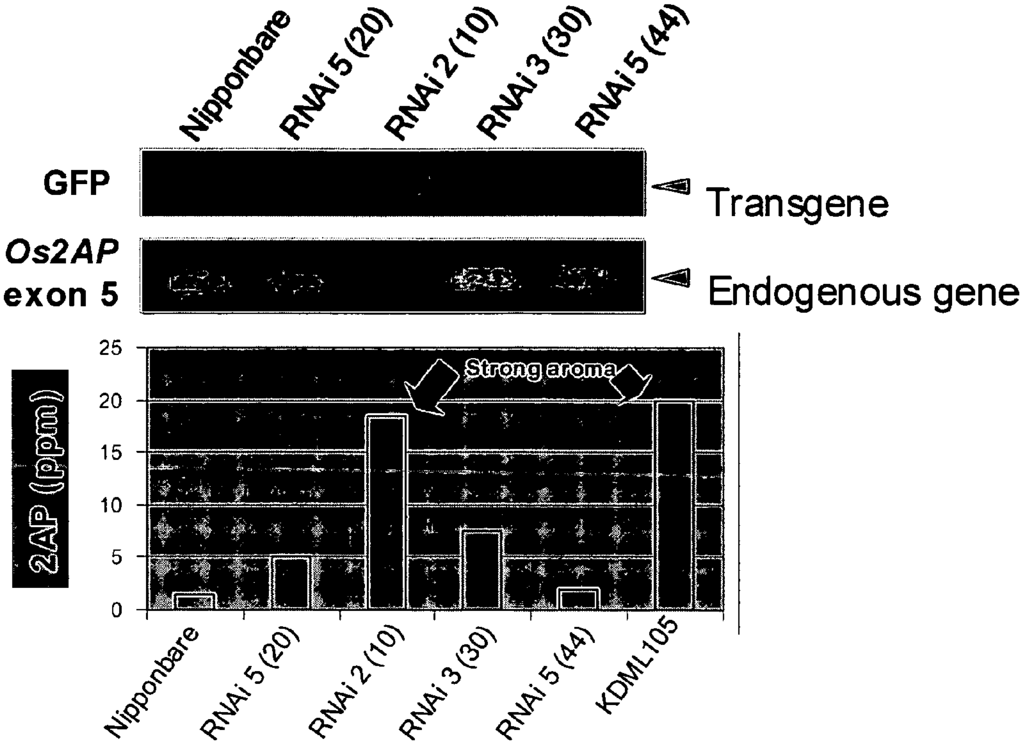

FIG. 7B depicts expression of the RNAi construct, GFP, and the endogenous Os2AP. The lower panel shows 2-acetyl-1-pyrroline levels and aroma. Os2AP-RNAi2 is an RNAi construct against the Os2AP gene.

FIG. 8A depicts the results from screening F6 progeny for the Os2AP variant correlated with increased aroma using the "Aromarker" primer set.

Figure 8B:
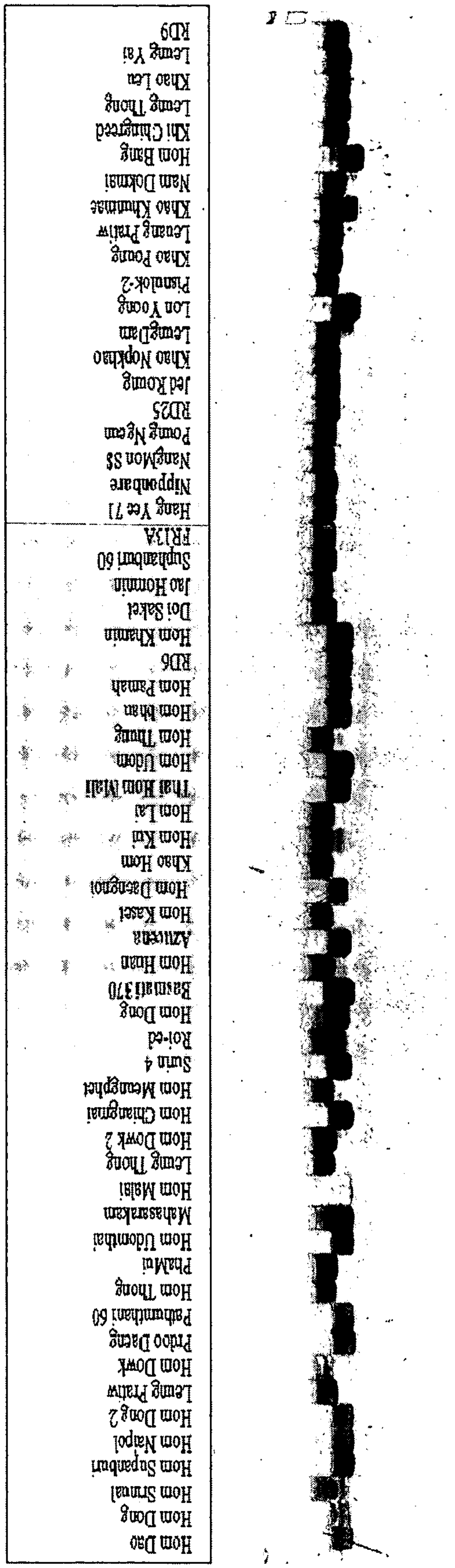

FIG. 8B depicts the results from screening various varieties of rice for the aromatic Os2AP allele.

FIG. 9A shows the DNA sequences of the Os2AP orthologs from various strains of rice. The nucleotide sequences in the alignment include nucleotides 701 to 765 from SEQ ID NO: 5 and nucleotides 701-757 from SEQ ID NO: 2, SEQ ID NO: 5, and SEQ ID NOS: 89-95.

Figure 9B:
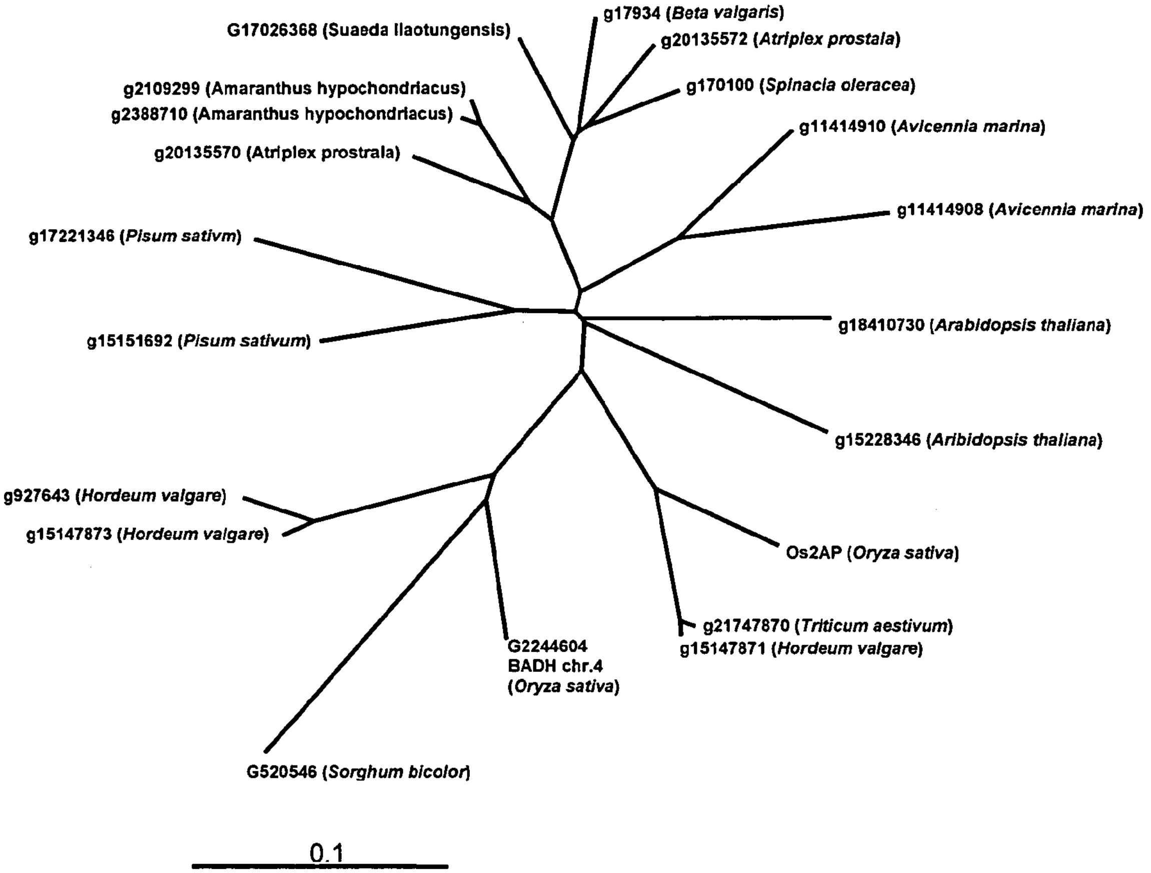

FIG. 9B shows the phylogenetic tree constructed using Neighbor-Joint tree of 22 orthologs of BADH and Os2AP.

BRIEF DESCRIPTION OF SOME OF THE SEQUENCES IN THE SEQUENCE LISTING

SEQ ID NO: 1 is the genomic nucleotide sequence of the Os2AP gene from an aromatic rice strain, Thai Hom Mali.

SEQ ID NO: 2 is the protein-encoding nucleotide sequence of Thai Hom Mali Os2AP.

SEQ ID NO: 3 is the amino acid sequence of the Thai Hom Mali Os2AP protein.

SEQ ID NO: 4 is the genomic nucleotide sequence of the Os2AP gene from a non-aromatic rice strain, Nipponbare.

SEQ ID NO: 5 is the protein-encoding nucleotide sequence of Nipponbare Os2AP.

SEQ ID NO: 6 is the amino acid sequence of Nipponbare Os2AP protein.

SEQ ID NO: 7 through 88 are primers which can be used to amplify portions of the Os2AP nucleotide sequence, GFP, or actin. (TABLE 1).

SEQ ID NO: 89 through 95 are sequences of fragments of Os2AP gene orthologs.

SEQ ID NO: 96 is the decapeptide which is highly conserved among general aldehyde dehydrogenases.

DETAILED DESCRIPTION OF THE INVENTION

The invention relates to Os2AP genes. Nucleic acid sequences from Os2AP genes are used to enhance the levels of 2-acetyl-1-pyrroline, a major aromatic compound found in rice, wheat, maize, oat, pandan leaf, aromatic coconut, and some bacteria and fungi.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987); Plant Breeding: Principles and Prospects (Plant Breeding, Vol 1) M. D. Hayward, N. O. Bosemark, I. Romagosa; Chapman & Hall, (1993.); Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995), Harlow and Lane, eds. (1988) ANTIBODIES, A LABORATORY MANUAL, and ANIMAL CELL CULTURE R. I. Freshney, ed. (1987).

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y. Definitions of common terms in plant biology may be found in Esau, Plant Anatomy, published by John Wiley & Sons (1977) (ISBN 0-471-24520-8); and Solomon et al., Biology, published by Saunders College Publishing (1993).

DEFINITIONS

In order to facilitate review of the various embodiments of the invention, the following definitions are provided:

Os2AP polynucleotide sequence: The genes according to the subject invention include not only the full-length sequences disclosed herein but also fragments of these sequences, which retain the characteristic activity of the sequences specifically exemplified herein.

The rice Os2AP gene sequence is disclosed herein. It is apparent to a person of skill in this art that Os2AP polynucleotide sequences from another plant can be readily identified and obtained through several means using the rice Os2AP gene sequence. The specific genes, or portions thereof, may be obtained from a culture depository, or constructed synthetically, for example, by use of a gene machine.

Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Various enzymes may be used to directly obtain active fragments of these Os2AP polynucleotide sequences.

Equivalent Os2AP polynucleotide sequences and/or genes encoding these equivalent Os2AP polynucleotide sequences can also be isolated from strains and/or DNA libraries using the teachings provided herein. For example, antibodies to the Os2AP proteins disclosed herein can be used to identify and isolate other Os2AP proteins from a mixture of proteins. Specifically, antibodies may be raised to the portions of the Os2AP proteins which are most constant and most distinct from other proteins. These antibodies can then be used to specifically identify equivalent Os2AP proteins with the characteristic activity by immunoprecipitation, enzyme linked immunoassay (ELISA), or Western blotting.

A further method for identifying the genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying genes of the subject invention. Exemplary probes are described in Table 1.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the Os2AP proteins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of an Os2AP polynucleotide sequence encoding a gene of the invention. Such mutants can be made by techniques well known to persons skilled in the art. For example, UV irradiation can be used to prepare mutants of host organisms, tDNA insertion mutagenesis can be used, or TILLING (Targeted Induced Local Lesion of Genome) can be used. Likewise, such mutants may include asporogenous host cells which also can be prepared by procedures well known in the art.

Os2AP polynucleotide sequences, including those from rice, may be obtained using the PCR primers of the invention. These primers are shown in TABLE 1, and correspond to the sequences depicted in SEQ ID NO: 7 through SEQ ID NO: 79. Combinations of these primers may be used to amplify different regions of the Os2AP gene. PCR conditions which work for this amplification are as follows: 10 μL reaction mixture with 10 ng of template DNA, 0.1 mM dNTP, 0.5 (M of each primer, 0.5 unit of Taq polymerase, 2.0 mM MgCl2, and 1× Thermophilic Polymerase Buffer (Promega). This mixture should undergo 30 cycles of PCR with the following times and temperatures: 94° C. for 30 seconds (denaturation), 60° C. for 30 seconds (annealing), and 72° C. for 2 min (extension).

TABLE 1

List of primers

| SEQ ID NO: | Primer name | Sequence (5'→3') |
|---|---|---|
| 7 | OS2AP-8L | GCCATGCCAACTGAGTAAAG |
| 8 | OS2AP-8R | CAATTTTATTCGCTCTGTGC |
| 9 | OS2AP-9L | TGCAACATCGCGTCTTATTC |
| 10 | OS2AP-9R | GCAACTAGCAAGAGCATACACC |
| 11 | OS2AP-12L | ACCTGACATCATGCCTTTGG |
| 12 | OS2AP-12R | CCGGTCATCAGCTAACTTCC |
| 13 | OS2AP-13R | CCCTTCGTCATAAAATATACTAGCAA |
| 14 | OS2AP-14L | TCCTCCAACATGCTCTTTCG |
| 15 | OS2AP-14R | CAGAGAAGTTTACGCCGTTG |
| 16 | OS2AP-15L | TTTTTAAATAAGATGAACGGTCAAA |
| 17 | OS2AP-16L | CTCTCCACCCTCTGCTTCTG |
| 18 | OS2AP-16R | CTCTCCGCTTGAACCCATC |
| 19 | OS2AP-17L | GCATGGCTGATTGTGTATCTG |
| 20 | OS2AP-17R | TTCCAAACCTACGGACAAAAG |
| 21 | OS2AP-18L | TTCCTCTTCTCTTGTGCAAAC |
| 22 | OS2AP-18R | CACGGAAGCCAATTCAGATG |
| 23 | OS2AP-19L | CTATCCTCTCCTGATGGCAAC |
| 24 | OS2AP-19R | TGGCTACTAGAATGATGCTCAAAG |
| 25 | OS2AP20L | CCTTTTGTGTCGCTTTTGAG |
| 26 | OS2AP20R | AAAATAGCCTTCACTCGTTGC |
| 27 | OS2AP21L | CCATCGATTTCGAGGGTAAC |
| 28 | OS2AP21R | CGCATCCGATAATATGTTG |
| 29 | OS2AP22L | GTAATTAGGAGTACGACTCTCGTC |

TABLE 1-continued

List of primers

| SEQ ID NO: | Primer name | Sequence (5'→3') |
|---|---|---|
| 30 | OS2AP22R | GCTTATAGCCTACTGTATCCTCCTC |
| 31 | OS2AP23L | AATTGGTTAACCCAGCAAGC |
| 32 | OS2AP23R | ACATTGTGAAACGGAGGAAG |
| 33 | OS2AP24L | GCTATAAGCCAGCTGCAAAC |
| 34 | OS2AP24R | GCAGTTGGTACGGACTTCG |
| 35 | OS2AP25L | CCTAAATATTTGACGCCGTTG |
| 36 | OS2AP25R | TGAAGAGGAGGGTACCGATG |
| 37 | OS2AP26L | CACCACTCCACACCTGACAC |
| 38 | OS2AP26R | GTACGGAACACACGCACAAG |
| 39 | OS2AP27L | TGTTGTTGTTGTTGCTGCTG |
| 40 | OS2AP27R | GCCGTGAGCCATATACACTTG |
| 41 | 023088C02 1L | AGCTCCAGCTCCTCCTCGAT |
| 42 | 023088C02 2L | TATCTCTCACCGACCCCAAA |
| 43 | 023088C02 2R | TGTTGCCATCAGGAGAGGA |
| 44 | 023088C02 3R | CTCTTGATGAAGCAGCATGG |
| 45 | 023088C02 3R | CCCAGTAAATGCAACCTTGTC |
| 46 | 023088C02 4R | GGCAACATGGAAGGTAGCTC |
| 47 | 023088C02 4R | CCATGCAACCATCCTTTCTT |
| 48 | 023088C02 5R | TTATGGCTTCAGCTGCTCCT |
| 49 | 023088C02 5R | CAATGGCTTCTTCTTCAGTGC |
| 50 | 023088C02 6R | GCCCGTTGTTAGTGAAGGAC |
| 51 | 023088C02 6R | GTACCATCCCCACGGCTCAT |
| 52 | 023088C02 7L | CGAGCGATGCCAGAGATTA |
| 53 | 023088C02 7R | AGCACATGGCAAATCAAACA |
| 54 | OS2AP-exon 7.1-del_F | TGCTCCTTTGTCATCACACC |
| 55 | OS2AP-exon 7.1-del_R | TTTCCACCAAGTTCCAGTGA |
| 56 | OS2AP_in1L | TTCGCTGCAGAACAGATGAC |
| 57 | OS2AP_in1R | CTGATGGTTACGCGACAATTT |
| 58 | OS2AP_inTA2L | ATTTGAACCGGGACAGAACA |
| 59 | OS2AP_inTA2R | TTTTGATGTGCCCTCTCCTT |
| 60 | OS2AP_inAAT3L | TGGGTAATCTTGTTCTGGAG |
| 61 | OS2AP_inAAT3R | AGTGCCAAATGCATGCTAGA |
| 62 | OS2AP_inG4L | TGGGGCTCAAAAACCTACTG |
| 63 | OS2AP_inG4R | GTCCGGGCCAAGTACCTC |
| 64 | OS2AP-5-UTR-EX1-5 F | ATCTCTCACCGACCCCAAAT |

TABLE 1-continued

List of primers

| SEQ ID NO: | Primer name | Sequence (5'→3') |
|---|---|---|
| 65 | OS2AP-5-UTR-EX1-5 R | CCATTGGAAGAGAGACAGGTG |
| 66 | OS2AP-ATG1-600 F | TGTTGTTGTTGTTGCTGCTG |
| 67 | OS2AP-ATG1-600 R | TGGGGCTCAAAAACCTACTG |
| 68 | OS2AP-EX5-12 F | GGTTGGTCTTCCTTCAGGTG |
| 69 | OS2AP-EX5-12 R | GGTCCAAAAGCAACCAAAGA |
| 70 | Aromarker BigL | ACTGGTAAAAAGATTATGGC |
| 71 | Aromarker BigR | CAAGCCGATCAACCAGTACA |
| 72 | Aromarker SmallL | CCATGCTGCAAGCAATGTA |
| 73 | Aromarker SmallR | AACCATAGGAGCAGCTGAAATA |
| 74 | OS2AP8_OUT_F | ACCCTGGTGTAGACAAGGTA |
| 75 | OS2AP8_IN_F | GGGAGTTATGAAACTGGTATAT |
| 76 | OS2AP8_IN_R | ATAGGAGCAGCTGAAGCCAT |
| 77 | OS2AP8_OUT_R | GTCCCGCACTTCAGAATTAG |
| 78 | OS2AP8_ex2_F | CTCTGCTTCTGCCTCTGATT |
| 79 | OS2AP-exon9.1-del_RN | CTGGCTACTAGAATGATGCTC |
| 80 | Exon6to9NcoIF | AATTCCATGGGGTTGGTCTTCCTTCAGGTG |
| 81 | Exon6to9SpeIR | AATTACTAGTTTCCACCAAGTTCCAGTGAA |
| 82 | Exon6to8NheIR | AATTCCATGGGGTTGGTCTTCCTTCAGGTG |
| 83 | GFPU | CTTGTTGAATTAGATGGTGATGTT |
| 84 | GFPL | GTTGTGGGAGTTGTAGTTGTATTC |
| 85 | Os2APCH4U | TAGCTTCACATCCCCATGTG |
| 86 | Os2APCH4L | GCACCTTCACATCTTGCTGT |
| 87 | ActinU | ACATCGCCCTGGACTATGAC |
| 88 | ActinL | TGCTGAGAGATGCCAAGATG |

Os2AP homologs: Sequences that show similarity to those described in this application can be identified by computer-based methods, using public domain sequence alignment algorithms and sequence similarity search tools to search sequence databases (public domain databases include Genbank, EMBL, Swiss-Prot, PIR and others).

Similarity searches retrieve and align sequences for comparison with a target sequence to be analyzed (i.e., a query sequence). The optimal alignment between local regions of the compared sequences is known as a local alignment. Sequence comparison algorithms use scoring matrices to assign an overall score to each of the alignments.

Polynucleotide and polypeptide sequences may be aligned, and percentage of identical residues in a specified region may be determined against other polynucleotide and polypeptide sequences, using computer algorithms that are publicly available. The percentage identity score is dependent on the length of the overlap region of the sequences being compared.

The similarity between two nucleic acid sequences or two amino acid sequences may be expressed in terms of sequence identity (or, for proteins, also in terms of sequence similarity). Sequence identity is frequently measured in terms of percentage identity; the higher the percentage, the more similar the two sequences are. As described herein, homologs and variants of the Os2AP protein-encoding nucleic acid molecules may be used in the present invention. Homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. In addition, such sequences hybridize to homologous sequences under high stringency conditions. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

The alignment may include the introduction of gaps in the sequences to be aligned. In addition, for sequences which contain either more or fewer amino acids than the protein depicted in SEQ ID NO: 3 or SEQ ID NO: 6, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Proteins can be classified according to their sequence relatedness to other proteins in the same genome (paralogs) or a different genome (orthologs). Ortholog genes are genes that evolved by speciation from a common ancestral gene. These genes normally retain the same function as they evolve. Paralog genes are genes that are duplicated within a genome. These genes may acquire new specificities or modified functions which may be related to the original one. Phylogenetic analysis methods are well-known to those with ordinary skill in bioinformatics.

As will be appreciated by those skilled in the art, the sequences of the present invention may contain sequencing errors. That is, there may be incorrect amino acid sequences, nucleotides, frameshifts, unknown nucleotides, or other types of sequencing errors in any of the sequences; however, the correct sequences will fall within the homology and stringency definitions herein for nucleic acids, and the protein homology described for proteins or polypeptides.

Os2AP polypeptide: As used herein, the term "Os2AP polypeptide" means a gene product having substantially the amino acid sequence of an Os2AP ortholog. An Os2AP polypeptide is characterized, in part, in that a decrease in its expression, reduction in its mRNA levels, or reduction in protein amount or activity results in an increase in the levels of the compound 2-acetyl-1-pyrroline in the plant. An Os2AP polypeptide also is characterized, in part, by having an amino acid sequence with at least about 30%, 40%, 50%, 60%, 70%, 80%, 90% or 95% amino acid identity with the amino acid sequence depicted in SEQ ID NO: 3 or SEQ ID NO: 6.

Substantially identical: By "substantially identical" is meant a polypeptide or nucleic acid exhibiting at least 30%, preferably 50%, more preferably 80%, and most preferably 90%, or even 95% homology to a reference amino acid sequence (for example, the amino acid sequence depicted in SEQ ID NO: 3 or SEQ ID NO: 6) or nucleic acid sequence (for example, the nucleic acid sequence depicted in SEQ ID NO: 1, SEQ ID NO: 2, SEQ ID NO: 4 or SEQ ID NO: 5). For polypeptides, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, or PILEUP/PRETTYBOX programs). For example, such software when set to standard parameters matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Elevated level: Elevated level, as used herein, means an increase in the average level of the compound 2-acetyl-1-pyrroline in a non-naturally occurring plant when compared to the average level of the compound 2-acetyl-1-pyrroline in the corresponding naturally occurring plant. Given that the level of the compound 2-acetyl-1-pyrroline in a plant will vary from plant to plant depending upon a number of variables, one of skill in the art would understand that in comparing the average level of the compound 2-acetyl-1-pyrroline in a non-naturally occurring plant and the corresponding naturally occurring plant, a reasonably sized sample population of each type of plant grown under similarly controlled conditions should be compared. The level of the compound 2-acetyl-1-pyrroline is preferably measured in several plants from each population and averaged to determine whether the non-naturally occurring plant contained an elevated level. The elevated level in the non-naturally occurring plant of the present invention is, on average, at least about 20% greater, 40% greater, 60% greater, 80% greater, 100% greater, 150% greater, 200% greater, 250% greater, 300% greater, 400% greater, or 500% greater than in the corresponding naturally occurring plant.

Promoter: A recognition site on a DNA sequence or group of DNA sequences that provide an expression control element for a structural gene and to which RNA polymerase specifically binds and initiates RNA synthesis (transcription) of that gene.

Examples of plant expression constructs using these promoters are found in Fraley et al., U.S. Pat. No. 5,352,605. In most tissues of transgenic plants, the CaMV 35S promoter is a strong promoter (see, e.g., Odell et al., Nature 313:810, 1985). The CaMV promoter is also highly active in monocots (see, e.g., Dekeyser et al., Plant Cell 2:591, 1990; Terada and Shimamoto, Mol. Gen. Genet. 220:389, 1990). Moreover, activity of this promoter can be further increased (i.e., between 2-10 fold) by duplication of the CaMV 35S promoter (see e.g., Kay et al., Science 236:1299, 1987; Ow et al., Proc. Natl. Acad. Sci., U.S.A. 84:4870, 1987; and Fang et al., Plant Cell 1:141, 1989, and McPherson and Kay, U.S. Pat. No. 5,378,142).

Other useful plant promoters include, without limitation, the nopaline synthase (NOS) promoter (An et al., Plant Physiol. 88:547, 1988 and Rodgers and Fraley, U.S. Pat. No. 5,034,322), the octopine synthase promoter (Fromm et al., Plant Cell 1:977, 1989), figwort mosaic virus (FMV) promoter (Rogers, U.S. Pat. No. 5,378,619), and the rice actin promoter (Wu and McElroy, WO91/09948).

Exemplary monocot promoters include, without limitation, commelina yellow mottle virus promoter, sugar cane badna virus promoter, rice tungro bacilliform virus promoter, maize streak virus element, and wheat dwarf virus promoter.

Construct: Unless otherwise stated, the term "construct" refers to a recombinant genetic molecule comprising one or more isolated polynucleotide sequences of the invention.

Genetic constructs used for transgene expression in a host organism include a gene promoter sequence operably linked to an open reading frame and optionally a gene termination sequence 3' downstream of the open reading frame. The open reading frame may be orientated in either a sense or anti-sense direction, depending upon the intended use of the gene sequence. The construct may also include selectable marker gene(s) and other regulatory elements for gene expression.

Vector: A DNA molecule capable of replication in a host cell and/or to which another DNA segment can be operatively linked so as to bring about replication of the attached segment. Plasmids, phagemids, cosmids, phage, virus, YACs, and BACs are all exemplary vectors.

The term "vector" refers to a nucleic acid molecule which is used to introduce a polynucleotide sequence into a host cell, thereby producing a transformed host cell. A "vector" may include genetic material in addition to the above-described genetic construct, e.g., one or more nucleic acid sequences that permit it to replicate in one or more host cells, such as origin(s) of replication, selectable marker genes and other genetic elements known in the art (e.g., sequences for integrating the genetic material into the genome of the host cell, and so on).

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

Electroporation: The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding. To effect transformation by electroporation one may employ either friable tissues such as a suspension culture of cells or embryogenic callus, or alternatively one may transform immature embryos or other organized tissues directly. One would partially degrade the cell walls of the chosen cells by exposing them to pectin-degrading enzymes (pectolyases) or mechanically wounding in a controlled manner. Such cells would then be receptive to DNA transfer by electroporation, which may be carried out at this stage, and transformed cells can then identified by a suitable selection or screening protocol dependent on the nature of the newly incorporated DNA.

Microprojectile Bombardment: A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly obtaining stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust some of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-Mediated Transfer: *Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agro-*

*bacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus using *Agrobacterium* vectors as described (Bytebier et al., 1987). Therefore, commercially important cereal grains such as rice, corn, and wheat must usually be transformed using alternative methods.

A transgenic plant formed using *Agrobacterium* transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for elevated 2-acetyl-1-pyrroline levels relative to a control (native, non-transgenic) or an independent segregant transgenic plant.

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below. As an example, a gene in a large genomic DNA fragment such as a contig is not sufficiently purified away from other biological components to be considered isolated due to the relatively large amount of extra DNA found in the average contig. As outlined below "recombinant nucleic acids" and "recombinant proteins" also are "isolated" as described above.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell; however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above. A gene in a large fragment such as a contig would not be a "recombinant nucleic acid" given that such artificial combination does not relate to the gene. However, if sequences around or within a gene in a contig have been manipulated for purposes relating to that gene (i.e., not merely because the gene is near the end of the contig), then such a gene in a contig would constitute a "recombinant nucleic acid" due to the relative proximity of the recombinant portion of the nucleic acid to the gene in question.

Non-naturally occurring plant: As used herein, the term "non-naturally occurring," when used in reference to a plant, means a plant that has been genetically modified by human intervention to alter the levels of the compound 2-acetyl-1-pyrroline in the plant. The naturally occurring plant that has been genetically modified is referred to as the "control" plant. Within the context of the invention, the control plant may be a transgenic plant. For example, the control plant may be an herbicide resistant transgenic plant. In this example, a non-naturally occurring plant would be herbicide resistant and would have elevated levels of the compound 2-acetyl-1-pyrroline compared to the control herbicide resistant plant. A transgenic plant of the invention, for example, is a non-naturally occurring plant that contains an exogenous nucleic acid molecule encoding an Os2AP gene or fragment thereof and, therefore, has been genetically modified by human intervention. In addition, a plant that contains a mutation in, for example, an Os2AP gene regulatory element or coding sequence as a result of calculated exposure to a mutagenic agent, such as a chemical mutagen, or an "insertional mutagen," such as a transposon or T-DNA, also is considered a non-naturally occurring plant, since it has been genetically modified by human intervention. In contrast, a plant containing only spontaneous or naturally occurring mutations is not a "non-naturally occurring plant" as defined herein. One skilled in the art understands that, while a non-naturally occurring plant typically has a nucleotide sequence that is altered as compared to a naturally occurring plant, a non-naturally occurring plant also can be genetically modified by human intervention without altering its nucleotide sequence, for example, by modifying its methylation pattern.

Transgenic plant: A plant or progeny thereof derived from a transformed plant cell or originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

I. The Os2AP Gene

A. Isolation of orthologs/homologs: The Examples section below, which describes the isolation and characterization of Os2AP genes in rice, is exemplary of a general approach for isolating Os2AP genes. Such Os2AP genes encode Os2AP proteins. The isolated genes can then be used to construct recombinant vectors for decreasing Os2AP gene expression in plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, Cold Spring Harbor Laboratory, Cold Spring Harbor, N.Y., (1989).

The isolation of an Os2AP gene may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaf, and a cDNA library which contains the Os2AP gene transcript is prepared from the mRNA. Alternatively, cDNA may be prepared from mRNA extracted from other tissues in which Os2AP genes or homologs are expressed.

The cDNA or genomic library can then be screened using a probe based upon the sequence of a cloned Os2AP gene such as the rice Os2AP genes disclosed here. Probes may be used to hybridize with genomic DNA or cDNA sequences to isolate homologous genes in the same or different plant species.

Nucleic acid molecules having sequence regions consisting of contiguous nucleotide stretches of 10-14, 15-20, 30, 50, or even of 100-200 nucleotides or so, identical or complementary to the DNA sequences depicted in SEQ ID NO: 1, SEQ ID NO: 2, SEQ ID NO: 4, or SEQ ID NO: 5 are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length of the complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating Os2AP polypeptide- or protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate Os2AP protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

Alternatively, the nucleic acids of interest can be amplified from nucleic acid samples using amplification techniques. For instance, polymerase chain reaction (PCR) technology can be used to amplify the sequences of Os2AP genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes Appropriate primers and probes for identifying Os2AP gene sequences from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990), incorporated herein by reference.

Polynucleotides may also be synthesized by well-known techniques as described in the technical literature. See, e.g., Carruthers et al., Cold Spring Harbor Symp. Quant. Biol. 47:411-418 (1982), and Adams et al., J. Am. Chem. Soc. 105:661 (1983). Double stranded DNA fragments may then be obtained either by synthesizing the complementary strand and annealing the strands together under appropriate conditions, or by adding the complementary strand using DNA polymerase with an appropriate primer sequence.

B. Organisms from which to isolate an Os2AP gene ortholog A broad range of plants and fungi can be used, including species from the genera *Zea, Avena, Hordeum, Secale, Triticum*, and *Sorghum*. 2-acetyl-1-pyrroline has been shown to be the major potent flavor compound of all aromatic rice, wheat and rye bread (Buttery et al., 1982, 1983), wet millet (Seitz et al., 1993), popcorn (Schieberle et al., 1991), *Bacillus cereus* (Romanczyk et al., 1995), and some fungal species such as *Aspergellus oryzae, Aspergellus awamori*, and *Sporobolus virginicus* (Nagsuk et al., 2004). There are several reports which show genome-wide synteny among cereals as well as a well-conserved proline metabolic pathway in plants and microorganisms (found online at the web page for the Kyoto Encyclopedia of Genes and Genomes, Kyoto University, Bioinformatics Center, Institute for Chemical Research). Therefore, orthologs of the Os2AP gene may act in a comparable fashion among cereal plants, and the teachings provided in this invention can enhance the accumulation of the compound 2-acetyl-1-pyrroline in other plants in a similar way as in rice.

II. Reduction of Os2AP Gene Expression or Os2AP Protein Levels or Activity to Increase 2-Acetyl-1-Pyrroline Levels in Plants A. Mutagenesis Chemical mutagens such as EMS (methanesulfonic acid, ethyl ester) and both gamma ray and fast neutron radiation can create mutations in DNA. Some examples of mutations are deletions, insertions, and missense mutations. After mutation, screening can be done to identify deletions which create premature stop codons or otherwise non-functional Os2AP genes. Screening of mutants can be done by sequencing, or by the use of probes or primers specific to the Os2AP gene or protein, which are provided by the present invention. Specific mutations in Os2AP genes can also be created by TILLING (Targeted Induced Local Lesion of Genome) (Till et al., 2003) and tDNA insertion. Such mutations can result in decreases in Os2AP gene expression, decreased stability of Os2AP mRNA, or decreased activity and/or stability of the Os2AP protein. Such plants as defined herein are non-naturally occurring.

B. Antisense technology Antisense technology prevents the translation of target mRNA, such as Os2AP mRNA. As such, antisense technology generally reduces the levels of the target protein, here the Os2AP protein. The Os2AP gene or fragments thereof can be introduced into the plant in antisense orientation. The fragments can be as small as 18 nucleotides and as large as 3,000 nucleotides or larger. cDNA fragments of an Os2AP gene can be cloned into a vector (for example, pCAMBIA1302) in the opposite orientation as the native gene. The inverted transcript will form a heteroduplex structure with the native Os2AP gene transcript, which is then degraded before translation. The sense and antisense sequences need not be identical, even partial homology can be sufficient to achieve suppression of target gene expression. So, a sequence from rice Os2AP (SEQ ID NO: 1, SEQ ID NO: 2, SEQ ID NO: 4 and SEQ ID NO: 5) can be used to suppress Os2AP gene expression in other plants, without knowing the sequence of the Os2AP gene orthologs from that plant.

C. RNA interference: RNA interference (RNAi) is another technique which pertains to elimination of target mRNA. There are variations in the construction of vectors for RNAi, but the basic result is the formation of a hairpin loop structure in the RNA (Horiguchi 2004) In Example 2a fragment of Os2AP nucleotide sequence encompassing exons 6, 7, and 8 in the opposite direction to its cDNA was cloned into a vector to result in an inverted hairpin structure in the mRNA. These hairpin structures are cleaved into small fragments by an endonuclease named Dicer, whose function is to prevent erroneous transcripts from being translated (Hamilton and Baulcombe, 1999, Matzke et al., 2001). The small fragments of mRNA are generally about 20 to 21 nucleotides in size, and have been termed siRNAs, or small interfering RNAs. Larger and smaller fragments can also be utilized. These siRNAs can downregulate the expression of homologous genes. Again, the homology need not be complete, so sequences from rice detailed in this invention could be used to create RNAi constructs for other plants. Example 2 shows how an RNAi experiment targeting the Os2AP gene in a non-aromatic rice strain resulted in elevated 2-acetyl-1-pyrroline levels, and fragrance, to a level found in aromatic rice.

III. Creation of Transgenic Plants

To use isolated Os2AP gene sequences in the previous techniques, recombinant DNA vectors suitable for transformation of plant cells can be prepared. Techniques for transforming a wide variety of higher plant species are well known and described in the technical and scientific literature. See, for example, Weising et al. Ann. Rev. Genet. 22:421-477 (1988).

Such DNA constructs may be introduced into the genome of the desired plant host by a variety of conventional techniques. For example, the DNA construct may be introduced directly into the genomic DNA of the plant cell using techniques such as electroporation, PEG poration, particle bombardment and microinjection of plant cell protoplasts or embryogenic callus, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. Embo J. 3:2717-2722 (1984). Electroporation techniques are described in Fromm et al. Proc. Natl. Acad. Sci. USA 82:5824 (1985). Ballistic transformation techniques are described in Klein et al. Nature 327:70-73 (1987). Using a number of approaches, cereal species such as rye (de la Pena et al., Nature 325: 274-276 (1987)), corn (Rhodes et al., Science 240:204-207 (1988)), and rice (Shimamoto et al., Nature 338:274-276 (1989) by electroporation; Li et al. Plant Cell Rep. 12:250-255 (1993) by ballistic techniques) can be transformed.

*Agrobacterium tumefaciens*-meditated transformation techniques are well described in the scientific literature. See, for example Horsch et al. Science 233:496-498 (1984), and Fraley et al. Proc. Natl. Acad. Sci. USA 80:4803 (1983). Although *Agrobacterium* is useful primarily in dicots, certain monocots can be transformed by *Agrobacterium*. For instance, *Agrobacterium* transformation of rice is described by Hiei et al., Plant J. 6:271-282 (1994).

Transformed plant cells which are derived by any of the above transformation techniques can be cultured to regenerate a whole plant which possesses the transformed genotype, and thus an elevated level of 2-acetyl-1-pyrroline and increased aroma. Such regeneration techniques rely on manipulation of certain phytohormones in a tissue culture growth medium, typically relying on a biocide and/or herbicide marker which has been introduced together with the Os2AP nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. Ann. Rev. of Plant Phys. 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

IV. Testing for 2-acetyl-1-Pyrroline Levels

A. Sensory evaluation The volatile fragrance can be sensed from dry seeds, cooked rice, or ground leaves. (Dhulappanavar, 1976, Ghose et al., 1952, Kadam et al., 1938). Such sensing includes taste testing. Another popular practice among rice breeders is to heat leaf tissue in water followed by application of a solution of dilute KOH (Sood and Siddiq, 1978). These tests are not always consistent and reliable, and are prone to human error and preference.

Figure 1:
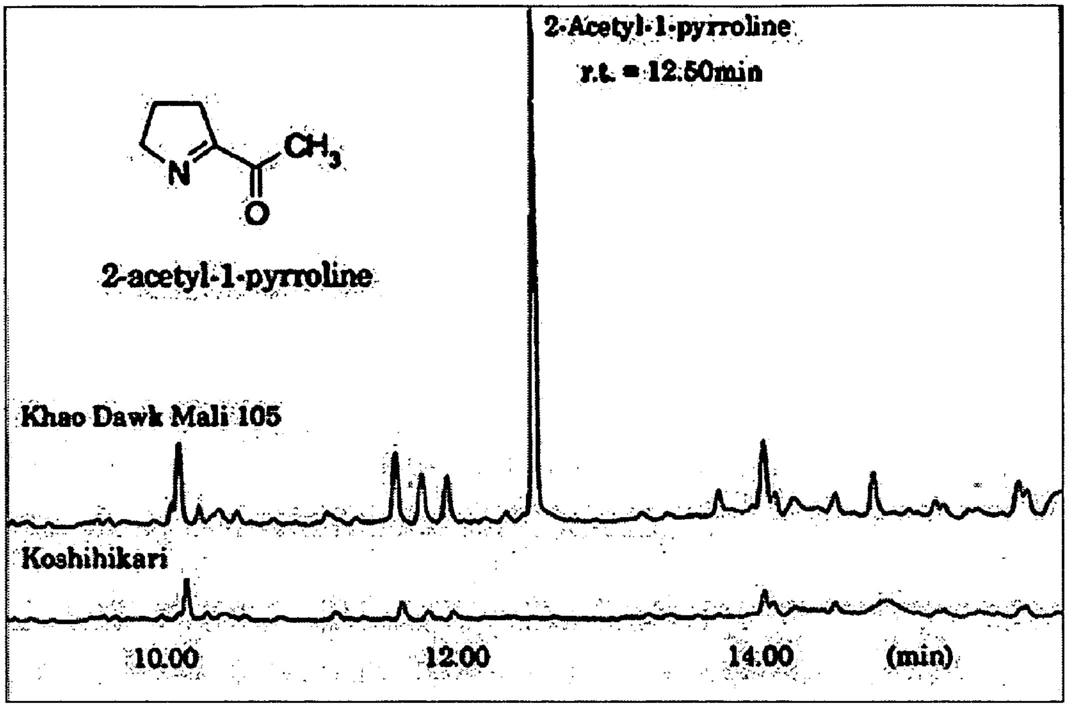
FIG. 1 depicts the chemical structure of 2-acetyl-1-pyrroline from GC-MS extracted from Khao Dawk Mali (KDML105), the Thai Jasmine rice (aromatic), and Koshihikari, a non-aromatic rice.

B. Chromatography: A more reliable method using gas chromatography was created for quantification of volatile compounds from 100 grams of cooked rice (Petrov et al., 1995). Recently, a gas chromatography/mass spectrometry (GCMS) technique was developed to analyze 2-acetyl-1-pyrroline levels as low as 1 part per billion from only one gram of rice (Mahatheeranont et al., 1995). As such, GCMS can be utilized to test levels of 2-acetyl-1-pyrroline in naturally occurring and non-naturally occurring plants. See FIG. 1.

DESCRIPTION OF PREFERRED EMBODIMENTS

Example 1

Positional Cloning of Gene Controlling Aroma in Rice

The rice aroma trait had been previously mapped onto chromosome 8 based on both qualitative and quantitative aroma determination methods (Lorieux et al. 1996). The aroma gene has been mapped at 4.5 cM away from RG28 (Ahn et al. 1992) and within 12 cM in between RG28 and RG1 (Lorieux et al. 1996). Recently, the single nucleotide polymorphism (SNP) marker RSP04 developed from the public rice genomic sequence has been mapped 2 cM away from the aroma gene (Jin et al. 2003).

The single QTL was located on the 4.5 cM region flanked by RFLP markers RG1 and RG28 on chromosome 8 (Lorieux et al., 1996; Lanceras et al. 2000). The EcoRI BAC library from KDML105 consisted of 75,264 clones representing 17 haploid genomes. An initial BAC contig consisting of twenty five BAC clones were selected by using six mapped markers within the region (Wanchana et al., 2005) and further refined using Hind III fingerprinting. To identify genes involved in the accumulation of 2-acetyl-1-pyrroline, the critical region was narrowed down using the following strategy.

Initially the single F6 plant that was segregating for grain aroma in F7 was selected as the source for generating new recombinants within the critical region. From F7 to F12, for each generation, heterozygous plants were selected based on both grain aroma and marker genotypes. In the F10 generation, the critical region was narrowed down to 380 kb by screening 374 F10 plants using eighteen polymorphic markers developed from KDML105 BAC end-sequences. The region was further refined to 120 kb by screening 274 F11 plants (FIG. 2). Based on graphical genotyping and the amount of 2-acetyl-1-pyrroline, 8 F11 plants were selected to generate aromatic, non-aromatic and heterozygous isogenic lines (FIG. 2). At this stage, three KDML BAC clones, 155L11, 68L13 and 167M23, were selected for shotgun sequencing. Alignment of the sequences from the KDML and corresponding Nipponbare genomic contigs resulted in the identification of 21 insertion/deletion ("indel") markers for further screening in the F12 generation. By using 1,116 F12 plants, the target region was narrowed down to 27 kb within the 58 kb BAC, 167M23 (FIG. 2). No further recombination was identified in this cross. Several pairs of isogenic lines were developed that clearly showed differences in 2-acetyl-1-pyrroline accumulation in rice grains (FIG. 6)

Sequence analysis revealed that the BAC 167M23 contains 19 genes. However, only ten genes have similarity to known proteins or coding sequences. Within the 27 kb region, three candidate genes were identified: 3-methycrotonyl-CoA carboxylase (MCCase), a hypothetical gene, and an unknown protein. Using 177 F6 plants from a cross between KDML105 and Jao Hom Nin (JHN), a non-aromatic black rice, a recombination site was identified within exon 7 of the unknown protein that affected grain aroma and 2-acetyl-1-pyrroline levels. To study the expression of these seven candidate genes from both BAC 167M23 and BAC 68L13, RT-PCR was performed during the grain filling period when 2-acetyl-1-pyrroline accumulates in rice grains. The total RNA was collected from rice panicles 10, 15 and 20 days after pollination from aromatic and non-aromatic isogenic lines. No expression was detected for the NBS/LRR gene. Most of the candidate genes did not show differential expression between the aromatic and non-aromatic isogenic lines. Only in the case of Os2AP, gene expression declined sharply in the aromatic isogenic lines 15 days after pollination (FIG. 3A). The decline in Os2AP gene expression was also pronounced in leaves, stems and roots (FIG. 3B). Therefore, both expression studies and positional cloning support Os2AP as the regulator responsible for accumulation of grain aroma and the synthesis of 2-acetyl-1-pyrroline in vivo.

Researchers had previously reported a single recessive nuclear gene controlling grain aroma (Berner and Hoff, 1986; Yanjuan et al., 1992; Ali et al., 1993). This is in accordance with the findings reported here. 2-acetyl-1-pyrroline accumulations were compared in aromatic and non-aromatic isogenic lines and the F1 plants. The results showed that 2-acetyl-1-pyrroline was not detected in F1 leaves. Because of segregation in the F2 generation, the 2-acetyl-1-pyrroline level was a quarter of the level found in the donor parents (FIG. 3C). Therefore, both classical and molecular genetics supported that the mutation in exon 7 is the molecular mechanism regulating 2-acetyl-1-pyrroline accumulation in planta.

The structures of the Os2AP genes were compared among KDML105, an aromatic isogenic line, a non-aromatic isogenic line, and Nipponbare. The 5.8 kb Os2AP gene consisted of 15 exons with several synonymous mutations found in exon 2 (FIG. 5A). For KDML105 and the aromatic isogenic lines, two important mutation events were identified in exon 7. First, two transitive mutations were found at positions 730 (A to T) and 732 (T to A), followed by the 8 base pair deletion 'GATTAGGC' starting at position 734. Analysis of 2-acetyl-1-pyrroline levels among 8 isogenic lines showed that the 8 base pair deletion is associated with the accumulation of 2-acetyl-1-pyrroline in rice grains (FIG. 6A). This mutation caused a frameshift translation start at position 729 and created the premature stop codon starting at position 753 (FIG. 5B). In Nipponbare, the Os2AP full-length cDNA is translated into 503 amino acids. The deletion created a truncated peptide of 252 amino acids (FIG. 5B). In the 177 F6 plants derived from KDML105 and JHN, double recombination flanking the 8 base pair deletion explains the failure to produce 2-acetyl-1-pyrroline in rice grains.

This premature stop codon may have significant effects on expression of Os2AP. Most mRNAs that contain a premature translational termination codon often fail to be translated. Consequently, they often trigger nonsense-mediated mRNA decay (NMD), a surveillance system whose function is to reduce errors in gene expression (Pulak and Anderson, 1993). This phenomenon may explain the low level of Os2AP gene expression in aromatic rice.

It is possible that Os2AP plays a role in the metabolic pathway of proline. The synthesis of glutamic acid from proline requires proline dehydrogenase (PropH) and delta-1-pyrroline-5-carboxylase dehydrogenase (P5CDH). During the grain filling period, expression of proline dehydrogenase was undetectable while Os2AP gene expression was up-regulated in non-aromatic isogenic lines. Therefore, it is possible that Os2AP replaces PropH in non-aromatic rice whereas in aromatic rice the degradation of Os2AP may shift the proline pool to be used for 2-acetyl-1-pyrroline synthesis. The isotopic labeling experiments also supported this hypothesis (Yoshihashi et al., 2002).

Example 2

Plant Transformation Using Os2AP Genes

The Os2AP gene was incorporated into an RNAi construct which was used to down regulate Os2AP gene expression and enhance 2-acetyl-1-pyrroline levels in rice.

Construction of Os2AP-ihpRNA containing vector A pCAMBIA1302 vector was used for expressing sense-antisense fragments of the Os2AP gene. Sense and antisense fragments were made by PCR using genomic DNA and total RNA from KDML105 as templates, respectively. A sense fragment-containing genomic DNA sequence corresponding to exons 6 through 9 was amplified with the primers containing NcoI and SpeI restriction sites (underlined) (forward: AATTCCATGGGGTTGGTCTTCCTTCAGGTG (SEQ ID NO: 80); reverse: AATTACTAGTTTCCACCAAGTTCCAGTGAA (SEQ ID NO: 81)). An antisense fragment containing a cDNA sequence corresponding to exons 6 through 8 was amplified with the primers containing NcoI and NheI restriction sites (forward: AATTCCATGGGGTTGGTCTTCCTTCAGGTG (SEQ ID NO: 80); reverse: AATTGCTAGCGGTCCAAAAGCAACCAAAGA (SEQ ID NO: 82). The PCR products were first digested with SpeI and NheI and subsequently ligated with T4 DNA ligase. The ligated fragments were then digested with NcoI. The purified ligated fragments were cloned into pCAMBIA1302 vector at the NcoI cloning site (FIG. 7A).

Rice transformation Embryogenic calli of a non-aromatic rice variety (*Oryza sativa* L. japonica variety Nipponbare) were used as target tissues for particle bombardment transformation (Nimlek, 1999). Hygromycin-resistant calli were screened by PCR using the primers Os2AP-exon 7.1-del_F and R (U: 5'-TGCTCCTTTGTCATCACACC-3' (SEQ ID NO: 54) and L: 5'-TTTCCACCAAGTTCCAGTGA-3' (SEQ ID NO: 55)) and primers for GFP (U: 5'-CTTGTTGAATTAGATGGTGATGTT-3' (SEQ ID NO: 83) and L: 5'-GTTGTGGGAGTTGTAGTTGTATTC-3' (SEQ ID NO: 84).

Southern blot analysis Total DNA was isolated from leaves of transgenic (R0) and control (Nipponbare) plants. Genomic DNA (10 mg) was digested with NcoI for detection of Os2AP-ihpRNA fragments. As a positive control, the DNA isolated form the plasmid Os2AP-RNAi was digested with NcoI. Following electrophoresis through a 0.8% agarose gel, DNA was transferred to Hybond-N+ Nylon membranes (Southern 1975). Hybridization with the probe was done according to the instructions of the manufacturer (Amersham). The radioactive probe was prepared by the random primer method using ($\alpha$-$^{32}$P)-dCTP. The probe consisted of the coding region of the Os2AP gene (SpeI-NcoI fragment of pOs2AP-RNAi, 210 nucleotides).

RT-PCR To investigate transcription levels at different growth stages and in different tissues, total RNA was extracted from young plants (10 days), adult leaves (30 day) and roots (14 days), and flowering panicles of Nipponbare and transgenic plants and used for RT-PCR analysis. The Os2AP gene aroma locus on chromosome 8 was amplified by PCR using the Os2AP-exon7.1 primers (U: 5'-TGCTC-CTTTGTCATCACACC-3' (SEQ ID NO: 54) and L: 5'-TTTCCACCAAGTTCCAGTGA-3' (SEQ ID NO: 55)). A homolog of the Os2AP gene on chromosome 4 also referred to as BADH (Os2AP-chr4; Genbank Accession No. AB001348) was amplified by PCR using Os2APch4 primers (U: 5'-TAGCTTCACATCCCCATGTG-3' (SEQ ID NO: 85) and L: 5'-GCACCTTCACATCTTGCTGT-3' (SEQ ID NO: 86) As a control, the rice actin gene (Genbank Accession No.: X16280) was amplified with ActinU: 5'-ACATCGC-CCTGGACTATGAC-3' (SEQ ID NO: 87) and ActinL: 5'-TGCTGAGAGATGCCAAGA TG-3' (SEQ ID NO: 88).

Real-time quantitative PCR Real-time quantitative PCR was performed by utilizing TAQMAN detection chemistry and the ABI PRISM 7700 Sequence Detection System (Applied Biosystems, Foster City, Calif., USA) according to the manufacturer's instructions. Relative amounts were calculated as the ratio of the copy number of Os2AP to that of rice actin. A TAQMAN detection probe was designed to differentiate between the aromatic and non-aromatic alleles of the Os2AP gene.

Results: Four hygromycin-GFP positive plantlets were regenerated. Expression of the GFP varied in the transgenic rice plants. $T_0$RNAi2 (10), the line with the best expression of the GFP, has the least expression of endogenous Os2AP (FIG. 7B). Analysis of 2-acetyl-1-pyrroline contents and sensory evaluation using the KOH method were well correlated. $T_0$RNAi2 (10) contained the highest amount of 2-acetyl-1-pyrroline and had the most aromatic leaves. $T_0$RNAi5(20) and $T_0$RNAi3(30), which express low amounts of the interfering sequence, accumulated less 2-acetyl-1-pyrroline and had lower aromatic leaf scores (FIG. 7B). Segregation analysis of grain aroma in $T_1$RNAi2 (10) confirmed this result. Therefore, the suppression of Os2AP gene expression by RNA interference enhances the accumulation of 2-acetyl-1-pyrroline in rice plants. This suggests that the natural suppression of Os2AP gene expression by NMD in aromatic rice caused by the 8 base pair deletion is the direct cause of aromatic rice aroma.

Example 3

Characterization of the Os2AP/BADH Loci of Rice

Os2AP is a homolog of BADH (betaine aldehyde dehydrogenase) previously found on chromosome 4 (Nagamura et al., 1997). We characterized the genomic sequence of the BADH gene from chromosome 4 and the Os2AP gene on chromosome 8 from the Genbank sequence accession numbers AB001348 and AP004463, respectively. According to gene annotation results from RiceGAAS (Rice Genome Automated Annotation System, from Sakata et al., 2002), the structural genes of both BADH and Os2AP comprise 15 exons interrupted by 14 introns. The ORFs encode proteins of 505 and 503 amino acid residues for BADH and Os2AP respectively. Both proteins are 77% identical at the amino acid level and share between 88% to 99% identity with other plant BADH proteins. Moreover, these two proteins contain nucleotide sequences encoding the decapeptide Val-Thr-Leu-Glu-Leu-Gly-Gly-Lys-Ser-Pro (SEQ ID NO: 96), which is highly conserved among general aldehyde dehydrogenases (Weretilnyk et al. 1990). According to Pfam analysis of the protein sequences, both BADH and Os2AP belong to the aldehyde dehydrogenase family. Proteins in this family have putative function in the synthesis of glycine betaine in certain plant species. However, in cereals like rice, maize, and wheat which do not accumulate glycine betaine, the function of these proteins is not known. We were surprised that pyrroline-5-carboxylate dehydrogenase (P5CDH), (Genbank Accession No. P30038) which functions in proline catabolism is also included in this family, since proline has been reported as the precursor of 2-acetyl-1-pyrroline. It is possible that the function of Os2AP is to catalyze the dehydrogenation of other aldehydes than betaine aldehyde.

Os2AP gene expression and rice aroma In order to identify whether Os2AP on chromosome 8 and BADH on chromosome 4 relate to aroma biosynthesis, the expression levels of aromatic and non-aromatic isogenic lines (whose genomic backgrounds were identical except for the aroma gene region) were analyzed. As a result, we found that BADH did not show differential expression between both isogenic lines, while Os2AP consistently showed gene suppression in all tissues of the aromatic isogenic lines (FIG. 3D). We also studied the expression of both proteins in isogenic lines and Nipponbare and K105 (aromatic strain). Os2AP gene expression was down regulated only in the aromatic isogenic lines and KDMLL105. In contrast, there was no detection of down regulation of Os2AP gene expression in the non-aromatic isogenic lines and Nipponbare rice (non-aromatic strain).

Example 4

Marker Assisted Selection

To develop new aromatic rice by conventional cross-breeding, one may cross an aromatic rice donor and a more productive recipient rice variety. The progeny from the cross will segregate for grain aroma among other traits. This situation confuses breeders and makes conventional breeding for better aromatic rice less successful. The discovery of the aroma gene will turn out to be a new paradigm for conventional breeders. Specific molecular markers can be developed to detect the aroma gene so that thousands of plants can be screened with the highest accuracy. DNA marker technology can allow breeders to detect the aromatic allele of the Os2AP gene at an early stage with high sensitivity. This leaves more opportunity for breeders to add preferred traits into aromatic plants at a later stage. The molecular basis of aroma identified in rice can possibly be found in other cereals and this will open ways to develop DNA markers for other cereals as well.

Example 5

Phylogenetic Analysis of Os2AP Gene

Proline biosynthesis is a highly conserved pathway in the plant kingdom. The biosynthesis of 2-acetyl-1-pyrroline proposed here may be a common theme utilized by other 2-acetyl-1-pyrroline-producing plants. To illustrate this point, the amino acid sequences of Os2AP genes were compared using multiple sequence alignment. The resulting phylogenetic tree shows that the Os2AP genes from rice, wheat and barley may share a common ancestor (FIG. 9B). Therefore, biosynthesis of 2-acetyl-1-pyrroline among cereals may share a common theme. Experiments with Os2AP gene orthologs in other cereals must be conducted in the future to illustrate this point.

It is interesting to trace back where the Os2AP gene came from. By scanning 95 landrace varieties using the "Aromarker" PCR primers, we found that the allele with the 8 base pair deletion correlates exactly with increased aroma. We also sequenced exon 7 for the 8 base pair deletion among wild species including *Oryza nivara* and *O. rufipogon* (FIG. 9A). We found that most aromatic varieties including Thai Jasmine, Basmati and Azucena have the deletion, and therefore share a common ancestor that may trace back to the ancient time. We identified the aromatic allele in aromatic wild rice as well. Therefore, a single mutation arose long before cultivation by humans to give rise to the aromatic rice we know today.

REFERENCES

The following references are hereby incorporated by reference in their entirety.

Abdullah et al., Biotechnology, 4:1087, 1986.

Ahn, S. N., C. N. Bollich and S. D. Tanksley. 1992. RFLP tagging of a gene for aroma in rice. Theor. Appl. Genet. 84: 825-828.

Ali, S. S., S. J. H. Jafri, M. G. Khan and M. A. Butt. 1993. Inheritance studies for aroma in two aromatic varieties of Pakistan. IRRN 18: 6.

Altschul, S. F. et al. (1990) J. Mol. Bio. 215:403-410.

Altschul, S. F. et al. (1994) Nat. Genet. 6(2):119-29.

Altschul S F, Gish W. Local alignment statistics. Methods Enzymol. 1996; 266:460-80.

Berner, D. R. and B. J. Hoff. 1986. Inheritance of scent in America long grain rice. Crop sci. 26: 876-878.

Buttery, R. G., L. C. Ling, B. O. Juliano, J. G. Turnbauhg. 1983. Cooked rice aroma and 2-acetyl-1-pyrroline. J. Agric. Food Chem: 823-826.

Buttery, R. G., L. C. Ling and O. B. Juliano. 1982. 2-acetyl-1-pyrroline: an important aroma component of cooked rice. Chem Ind (London). p. 958.

Callis and Walbot, Genes and Develop., 1:1183-1200, 1987.

Capecchi, "High efficiency transformation by direct microinjection of DNA into cultured mammalian cells," Cell, 22(2):479-488, 1980.

Clapp, "Somatic gene therapy into hematopoietic cells. Current status and future implications," Clin. Perinatol., 20(1): 155-168, 1993.

Corpet, F. (1988) Nucleic Acids Res. 16:10881-10890.

Cristou et al., Plant Physiol, 87:671-674, 1988.

Curiel, Agarwal, Wagner, Cotten. "Adenovirus enhancement of transferrin-polylysine-mediated gene delivery," Proc Natl. Acad. Sci. USA, 88(19):8850-8854, 1991.

Curiel, Wagner, Cotten, Bimstiel, Agarwal, Li, Loechel, Hu, "High-efficiency gene transfer mediated by adenovirus coupled to DNA-polylysine complexes," Hum. Gen. Ther., 3(2):147-154, 1992.

Dhulappanavar, C. V. 1976. Inheritance of scent in rice. Euphytica 25: 659-622

Eglitis and Anderson, "Retroviral vectors for introduction of genes into mammalian cells," Biotechniques 6(7):608-614, 1988.

Eglitis, Kantoff, Kohn, Karson, Moen, Lothrop, Blaese, Anderson. "Retroviral-mediated gene transfer into hemopoietic cells," Adv. Exp. Med. Biol., 241:19-27, 1988a.

Fraley et al., Bio/Technology. 3:629-635, 1985.

Fromm, Taylor, Walbot, "Expression of genes transferred into monocot and dicot plant cells by electroporation," Proc. Natl. Acad. Sci. USA, 82(17):5824-5828, 1985.

Fujimura et al., Plant Tissue Culture Letters, 2:74, 1985.

Fynan, Webster, Fuller, Haynes, Santoro, Robinson, "DNA vaccines: protective immunizations by parenteral, mucosal, and gene gun inoculations," Proc. Natl. Acad. Sci. USA 90(24):11478-11482, 1993.

Ghose, R. L. M. and W. T. Butany. 1952. Study on the inheritance of some characters in rice (*Oryza sativa* L.). Indian J. Genet. Plant Breed. 12: 26-30

Graham and van der Eb, "Transformation of rat cells by DNA of human adenovirus 5," Virology 54(2):536-539, 1973.

Hamilton, A. J. and Baulcombe, D. C. 1999. A species of small antisense RNA in posttranscriptional gene silencing in plants. Science 286: 950-952.

Higgins, D. G. and Sharp, P. M. (1988) Gene 73(1):237-44.

Higgins, D. G. and Sharp, P. M. (1989) Comput Appl Biosci. 5(2):151-3.

Horiguchi, G. 2004. RNA silencing in plants: a shortcut to functional analysis. Differentiation 72: 65-73.

Huang X. et al. (1992) Comput. Appl. Biosci. 8(2):155-65.

Jin, Q., D. Walters, G. M. Corderio, R. J. Henry and R. F. Reinke. 2003. A single nucleotide polymorphism (SNP) markers for fragrance in rice by analysis of the rice genome sequence. Mol. Breed. 9; 245-250.

Johnston and Tang, "Gene gun transfection of animal cells and genetic immunization," Methods Cell. Biol, 43(A): 353-365, 1994.

Jorgensen et al., Mol. Gen. Genet, 207:471, 1987.

Kadam, B. S. and V. K. Patankar. 1938. Inheritance of aroma in rice. India J. Genet. Breed. 40: 327-329

Kaiser et al., "Amphiphilic secondary structure: design of peptide hormones." Science, 223(4633):249-255, 1984.

Klee et al., Bio/Technology, 3:637-642, 1985.

Klein et al., Nature, 327:70, 1987.

Klein et al., Proc. Natl. Acad. Sci. USA, 85:8502-8505, 1988.

Kuby, In: Immunology 2nd Edition, W. H. Freeman & Company, NY, 1994.

Lanceras, J. C., Z. L. Huang, O. Naivikul, A. Vanavichit, V. Ruanjaichon and S. Tragoonrung. 2000. Mapping of genes for cooking and eating qualities in Thai jasmine rice (KDML 105). DNA Res 7: 93-101.

Lorieux, M., M. Petrov, N. Huang, E. Guiderdoni, A. Ghesquiere. 1996. Aroma in rice:

Genetic analysis of a quantitative trait. Theo. Appl. Genet. 93: 1145-1151.

Lorz et al., Mol. Gen. Genet., 199:178, 1985.

Lu, Xiao, Clapp, Li, Broxmeyer, "High efficiency retroviral mediated gene transduction into single isolated immature and replatable CD34(3+) hematopoietic stem/progenitor cells from human umbilical cord blood," J. Exp. Med, 178(6):2089-2096, 1993.

Maga, J. A. 1984. Rice product volatile: A review. J. Agric. Food. Chem. 32: 924-970.

Mahatheeranont, S., S. Promdang and A. Chaimpiriyakul. 1995. Volatile aroma compound of Khao Dawk Mali 105. Kasetsart J. (Nat. sci.) 29: 508-514

Maloy et al., In: Microbial Genetics, 2nd Edition, Jones and Bartlett Publishers, Boston, Mass., 1994.

Marcotte et al., Nature, 335:454, 1988.
Matzke, M. Matzke, A. J. M. and Kooter, J. M. 2001. RNA: Guiding gene silencing. Science 293: 1080-1083.
McCabe et al., Biotechnology, 6:923, 1988.
Nagamura Y, Antonio B A, Sasaki T. Rice molecular genetic map using RFLPs and its applications. Plant Mol Biol. 1997 September; 35(1-2):79-87. Review.
Nagsuk et al., 2004 Identification of 2-acetyl-1-pyrroline, the principal aromatic rice flavor compound in fungus cultures. Proceedings: The 2nd International Conference on Medicinal Mushroom and The International Conference on Biodiversity and Bioactive Compounds, 17-19 Jul., 2003, PEACH, Pattaya, Thailand, p 395-400.
Needleman, S. B. and Wunsch, C. D. (1970) J. Mol. Biol. 48:443-453.
Nimlek, E. 1999. Development of callus culture in four aromatic rices and gene transformation in Khao Dawk Mali 105. M.S. Thesis, Kasetsart University.
Omirulleh et al., Plant Molecular Biology, 21:415-428, 1993.
Paule, C. M. and Powers. 1989. Sensory and chemical examination of aromatic and nonaromatic rices. J. Food Sci. 54: 343-346.
Pearson W R. Using the FASTA program to search protein and DNA sequence databases. Methods Mol Biol. 1994; 24:307-31.
Pearson, W. R., Lipman, D. J., (1988) Proc Natl Acad Sci U.S.A. 85:2444-8.
Petrov, M., M. Danzart, P. Giampaoli, J. Faure, and H. Richard. 1995. Rice aroma analysis. Discrimination between a scented and a non-scented rice. Sci. Aliments 16: 339-352
Potrykus et al., Mol. Gen. Genet., 199:183, 1985.
Prokop and Bajpai, "Recombinant DNA Technology I," Ann. N.Y. Acad. Sci., Vol. 646, 1991.
Pulak R, Anderson P. "mRNA surveillance by the *Caenorhabditis elegans* smg genes".
Genes Dev. 1993 October; 7(10):1885-97.
Rogers et al., Methods Enzymol., 153:253-277, 1987.
Romanczyk, J. R. L. J, C. A. McClelland, L. S. Post and W. Martin Aitken. 1995. Formation of 2-acetyl-1-pyrroline by several *Bacillus cereus* strains isolated from cocao fermentation boxes. J. Agrc. Food chem. 43 (2): 469-475.
Sakata, K., Nagamura, Y., Numa, H., Antonio, B. A., Nagasaki, H., Idonuma, A., Watanabe, W., Shimizu, Y., Horiuchi, I., Matsumoto, T., Sasaki, T. & Higo, K.: "RiceGAAS: an automated annotation system and database for rice genome sequence", Nucleic Acids Res., 30: 98-102 (Jan. 2002)
Schieberle, P. 1991. Primary odorants in popcorn. J. Agric. Food Chem. 39 (6): 1141-1144.
Segal, In: Biochemical Calculations, 2nd Edition, John Wiley & Sons, New York, 1976.
Seitz, L. M., R. L. Wright, R. D. Waniska and L. W. Rooney. 1993. Contribution of 2-acetyl-1-pyrroline to odors from wetted ground pearl millet. J. Agric. Food Chem. 41(6): 955-958.
Smith, T. F. and Waterman, M. S. (1981) J. Mol. Biol. 147:195-197.
Sood, B. C., E. A. Siddiq. 1978. A rapid technique for scent determination in rice. Indian J. Genet. Plant Breed. 38: 268-271
Spielmann et al., Mol. Gen. Genet., 205:34, 1986.
P. Suprasanna, T. R. Ganaphthi, N. K. Ramaswamy, K. K. Surendranathan, P. S. Rao, Aroma synthesis in cell and callus cultures of rice, Rice Genet. Newsl. 15 (1998) 123-125.
P. Suprasarma, G. Bharati, T. R. Ganaphthi, V. A. Bapat, Aroma in rice: effects of proline supplementation and immobilization of callus cultures, Rice Genet. Newsl. 19 (2002) 9-11.
Takashi, T., T. Kurata and H. Kaio. 1980. Volatile components after cooking rice milled to different degrees. Agric. Biol. Chem. 44(4): 835-840.
Tanchotikul, U., and T. C. Y. Hsieh. 1991. An improved method for quantification of 2-acetyl-1-pyrroline, a "popcorn"-like aroma, in aromatic rice by high-resolution gas chromatography/mass spectrophotometry/selective ion monitoring. J. Agric. Food Chem. 39: 944-947.
Till, Bradley J. Reynolds, S H. Greene, E A. Codomo, C A. Enns, L C. Johson, J E. Burtner, C. Odden, A R. Yound, K. Taylor, N E. Henikoff, J G. Comai, L. and Henikoff, S. 2003. Large-scale discovery of induced point mutations with high-throughput TILLING. Genome Research 13:524-530
Toriyama et al., Theor. Appl. Genet., 73:16, 1986.
Uchimiya et al., Mol. Gen. Genet., 204:204, 1986.
Vasil et al., "Herbicide-resistant fertile transgenic wheat plants obtained by microprojectile bombardment of regenerable embryogenic callus," Biotechnology, 10:667-674, 1992.
Vasil, Biotechnology, 6:397, 1988.
Wagner, Zatloukal, Cotten, Kirlappos, Mechtler, Curiel, Bimstiel, "Coupling of adenovirus to transferrin-polylysine/DNA complexes greatly enhances receptor-mediated gene delivery and expression of transfected genes," Proc. Natl. Acad. Sci. USA, 89(13):6099-6103, 1992.
S. Wanchana, W. Kamolsukyunyong, S. Ruengphayak, T. Toojinda, S. Tragoonrung, A. Vanavichit, A rapid construction of a physical contig across a 4.5 cM region for rice grain aroma facilitates marker enrichment for positional cloning, Plant Sc. (in press).
Weretilnyk, E. and Hanson A. D. 1990. Molecular cloning of a plant betaine-aldehyde dehydrogenase, an enzyme implicated in adaptation to salinity and drought. Proc. Natl. Acad. Sci. 87: 2745-2749.
Wong and Neumann, "Electric field mediated gene transfer," Biochim. Biophys. Res. Commun. 107(2):584-587, 1982.
S. Wongpornchai, T. Sriseadka, S. Choonvisase, Identification and quantitation of the rice aroma compound, 2-acetyl-1-pyrroline, in bread flowers (Vallaris glabra Ktze), J. Agric. Food Chem. 51 (2003) 457-462.
Yajima, I., T. Yanai, and M. Nakamura. 1978. Volatile flavor components of cooked rice. Agric. Biol. Chem. 42: 1229.
Yamada et al., Plant Cell Rep, 4:85, 1986.
Yanjuan, D., H. Zhang and S. Shi. 1992. Genetic studies of aroma in the elite cytoplasmic male sterile (CMS) aromatic Japonica line shanghai A. Int. Rice Res Newsl. 17: 2.
Yoshihashi, T. 2002. Quantitative analysis on 2-acetyl-1-pyrroline of an aromatic rice by stable isotope dilution method and model studies on its formation during cooking. Food Sci. 67 (2): 619-622.
Zatloukal, Wagner, Cotten, Phillips, Plank, Steinlein, Curiel. Birnstiel, "Transferrinfection: a highly efficient way to express gene constructs in eukaryotic cells," Ann. N.Y. Acad. Sci., 660:136-153, 1992.

We claim:

1. A method for increasing aromatic fragrance in a transgenic rice plant comprising increasing the level of the compound 2-acetyl-1-pyrroline in a transgenic rice plant compared to its level in a control, non-transgenic rice plant by reducing the level of an mRNA in said rice plant, wherein the mRNA is encoded by a nucleic acid comprising SEQ ID NO: 5 and wherein the mRNA level is reduced by expression of said nucleic acid in an antisense orientation, or by expression of an RNA interference (RNAi) construct comprising at least a fragment of 20 contiguous nucleotides of said nucleic acid, said method further comprising the step of screening the resulting plants for an increase in popcorn-like aroma or for an increase in the compound 2-acetyl-1-pyrroline relative to said control, non-transgenic rice plant.

2. The method of claim 1, wherein said mRNA level of said nucleic acid is reduced by expressing said nucleic acid in the antisense orientation.

3. The method of claim 1, wherein said mRNA level of said nucleic acid is reduced by expressing said nucleic acid in a RNA interference (RNAi) construct.

4. The method of claim 1, wherein said RNAi construct comprises nucleotide 609 to nucleotide 867 of SEQ ID NO: 5.

* * * * *

SEQUENCE LISTING

<160> NUMBER OF SEQ ID NOS: 96

<210> SEQ ID NO 1
<211> LENGTH: 5857
<212> TYPE: DNA
<213> ORGANISM: Oryza sativa

<400> SEQUENCE: 1
atggccacgg cgatcccgca gcggcagctc ttcgtcgccg gcgagtggcg cgcccccgcg 60
ctcggccgcc gcctccccgt cgtcaacccc gccaccgagt cccccatcgg taccctcctc 120
ttcaccctct ccaccctctg cttctgcctc tgattagcct ttttgttgtt gttgttgttg 180
ctgctgtttt ttgcgtgtcg gtgcgcaagc gagatcccgg cgggcacggc ggaggacgtg 240
gacgcggcgg tggcggcggc gcgggaggcg cttaaaaaga acccgggccg cgactgggcg 300
cccgcgccgg gcgccgtccg ggccaagtac attcgcgcaa tcgctgacaa agtagggtgg 360
tgactaccct tatcagcctg cccgttttaa cgggagcctt gtgcgtgtgt tccgtacagg 420
gggaggagct ccgcgtggct ctccagtagg tttttgagcc ccaaatcgat cgatatgctc 480
tagttttaag tttgctgctt aaattcctca agggtttagt ttgcaaccaa atccttattt 540
tagcttcggt ataagccccc catatgatgt gcgtgcgtcg gcatcggaag tgcgtatcct 600
ctgttctgga ctaggaattg gccataggtt gatcgacagt tcgagtattc tgcttctgtt 660
tggaataagt tggaagcatg gctgattgtg tatctggatg ctgtttttgt ggtgattcgt 720
ttcaagctct tgttaattga tgggttcaag cggagagggt gcgcaacaac aagtgtatat 780
ggctcacggc catgggtgtg cacatttgat tggtgcgcaa caacaagtgt atattgtgtg 840
tgcttcgtta gttggcaggt cctagtcact aaatcactat tggattggta ctagctactt 900
ttgtgccttg acgatgggac tggattacta gccttttggt tgcctttgtg gtattccgtt 960
gttatgggcc tgttgatgga tggatccctt taatttctag tgccaaatgc atgctagatt 1020
tctcacagtt tttctcttca ggttatattt ctcgtatttc cttttcctaa aggattgctt 1080
tttcatgtat tttctggcat atataggtta ttattattat tattctccag aacaagatta 1140
cccatattat ggatcactag tgtacacttt tttggatgaa aaacctactt actgaaagta 1200
aaacagtgac cagtgcacac tttacttgaa ctgtcaaacc atcaattttc tagcaaagca 1260
ggggatgcta gccttccagt ctaaatgaca gtaaactact atacttttgt ccgtaggttt 1320
ggaaatatgc taatttctat cataaaaatt ttcatggcat atgcgagcat tttatgatca 1380
ccttttccct ttttcttcag ataatcgaga ggaaatctga gctggctaga ctagagacgc 1440
ttgattgtgg gaagcctctt gatgaagcag catgggacat ggtatgtggc cagttatcca 1500
ctgtatgaat atgtagttgc ctacacagca atctttcctg aacatgaatc ctgatgtatg 1560
atattccatt tgtcaggacg atgttgctgg atgctttgag tactttgcag atcttgcaga 1620
atccttggac aaaaggcaaa atgcacctgt ctctcttcca atggaaaact ttaaatgcta 1680
tcttcggaaa gagcctatcg gtgtagttgg gttgatcaca ccttggtatt tcacattttt 1740
ctctcatcct gcgcttatat ttatttatga cccaagcatg gtactaaata gtactagtaa 1800
catgcatata ctgaatgagt ttacaacttt acatgatttt tttgaactat gaaagttgaa 1860
gacatttgag attttattcc tcttctcttg tgcaaacata ttattgtctc acaaattgta 1920
cctagcagct actctctccg tttcatatta taagtcgttt gactttttc ctagtcaaaa 1980
tgtgttaagt ttgaccaagt ttatagaaaa atttagcaac atctaaaata tcaaagtcat 2040

-continued

```
gttttagtgt tttttcaggc tctcatgtaa gcaattttga tgtgccctct cctttcttct   2100
taatataatg atacacagct cttgtgtatt caaaggaata tatatatata tatatatata   2160
taatgataca cacctctcct ccgtgttaat gcagctcatt tgttctgtcc cggttcaaat   2220
atctattttt ctcatatgtt gtcagcatga ttcacttaat ttagtatata gaagatgcca   2280
ttatttatgt ctggaatctt actgcagaag ggaaaacaat tgataacgga attgattgca   2340
ttctaatttg ttgtttcttt gttatgttct tatcgacaat tacaaatttg attctgagaa   2400
tcatgttcgg gatgtgtatt tctactgcag gaactatcct ctcctgatgg caacatggaa   2460
ggtagctcct gccctggctg ctggctgtac agctgtacta aaaccatctg aattggcttc   2520
cgtgtaagtt taacatgtta acttgttaat gtcataccca tgctagttgc aatgacattt   2580
gattttaaaa tgttgtggca tgtccatgct gcaagcaatg taatttgaaa tctctctcta   2640
tcattaatta ccaggacttg tttggagctt gctgatgtgt gtaaagaggt tggtcttcct   2700
tcaggtgtgc taaacatagt gactggatta ggttctgaag ccggtgctcc tttgtcatca   2760
caccctggtg tagacaaggt acagctattc ctcctgtaat catgtatacc ccatcaatgg   2820
aaatgatatt cctctcaata catggtttat gttttctgtt aggttgcatt tactgggagt   2880
tatgaaactg gtatatattt cagctgctcc tatggttaag gtttgtttcc aaatttctgt   2940
ggatattttt tgttctcttt ctactaactc tctattatca attctcaatg ttgtcctttt   3000
cttttaactc ctttactttt tagaattgtg atcaagacac tttgagcatc attctagtag   3060
ccagttctat cctgtttctt acctttttat ggttcgtctt ttcttgacag cctgtttcac   3120
tggaacttgg tggaaaaagt cctatagtgg tgtttgatga tgttgatgtt gaaaaaggta   3180
catgccactt gctatgatta actaattctg aagtgcggga ctttgtaaag cacttaactg   3240
agctggatgc tagaccccca aaagcccttt ttggtgtctt gggcttgttg cagaaatact   3300
ggtcccagac gagcaggatg caagaaaatt aactactttt gccactgatt agtatttctt   3360
agaagttaca cctcaaggat tagcaatact ttcttaaaat gtgctattga ttaaaaagat   3420
gtcctgtatt attttgagca gatcttgtac tggttgatcg gcttgcatga aaatattgtt   3480
gaggattata atgccatgcc aactgagtaa agaaaagagt tgtaaaatat gttatgcaac   3540
atgaatatat atgtgatttc atttttcctt tttcttttcg tggcaaggaa ggcagttagg   3600
aaggactgat gtgaaaagca caagtactat tcttagttct ggaaaactgt gttctttatt   3660
ttcctaacta caattcacct tgattagtca gtaacttgat attggcaatt ctagctgatt   3720
atgaattctg tttatatttc actaattttg aatctttaat tacattttat ggttgaaatt   3780
taacgttttg tctggttatg gactctgttt gtattcactc aatttggatc ttccattaga   3840
tttcattgtt ggtccttctt cttgtacagc tgttgagtgg actctctttg gttgcttttg   3900
gaccaatggc cagatttgca gtgcaacatc gcgtcttatt cttcatgtaa gcattgaata   3960
tatccgtcaa tcataatcta ttgttgtact tgattttttt tctgatcaac tcctgagttc   4020
agattattat atgatgccat tactattgca cagagcgaat aaaattgtat ttatgcacag   4080
catgtatttt gagtaatata tgcattgcct attatttaat atatagattg tagcacttaa   4140
ttttgtgtcc atgtctctat gatgtttatt actttattat tgccggcatg aagcaacttt   4200
gaactctatg ttgatcttga actaaaattg aaattaattg gcttattgct attaatgata   4260
tagctttcag cttcttgctc ctgaccatga aagttttgca gaaaaaaatc gctaaagaat   4320
ttcaagaaag gatggttgca tgggccaaaa atattaaggt gtcagatcca cttgaagagg   4380
```

-continued

```
gttgcaggct tgggcccgtt gttagtgaag gacaggtacc acatgtaaac tttttctaaa   4440

ttcaaaaaag aaatgccact gatcaatggt aggtccttcc aagccttatt gctggattgt   4500

tgcactgttt tgtcaatttt gtgtaatata gttctgaatg aattagtcgg tgtatgctct   4560

tgctagttgc tagtatgtgg tacagggtct tcctactttg agcaaattcg tgttaaaatg   4620

cattgatgaa aaggccacct ttccgtaggt ttatcttgtc ataatttaaa ccccaataaa   4680

attttaattt tttgttttga ccccatggca ctttaatgaa atcacttagc catgagcttt   4740

tgtatatatt ttcaaagcac cagaatgttt agatggtttg ttggaaatct tacacatcct   4800

attgccttgt gtcagtatga gaagattaag caatttgtat ctaccgccaa aagccaaggt   4860

gctaccattc tgactggtgg ggttagaccc aaggtaataa tctactacac ggttgtatat   4920

ataggtaccc acatatcatt atgaagtaga aataatcttg tatgtttttg tcagcatctg   4980

gagaaaggtt tctatattga acccacaatc attactgatg tcgatacatc aatgcaaatt   5040

tggagggaag aagtttttgg tccagtgctc tgtgtgaaag aatttagcac tgaagaagaa   5100

gccattgaat tggccaacga tactcagtga gttttttttt taatacagtt cattgtcctg   5160

ttcaatcttg cagcatatgt atatactctg tggcatatga acttattctg ctactactac   5220

ttttgatagt tatggtctgg ctggtgctgt gctttccggt gaccgcgagc gatgccagag   5280

attaactgag gtatatccaa gtgaaggggg ttggcattgt ttgattcata tgacatggtt   5340

gcatcaagct gatattcaag aatctcattt attacttgca ttctatgcat ctccagttct   5400

tccctggact ccggtcaatg ttaatatagt ttgtttgcta gtagtatgct actccaatta   5460

agttgctctt cacttccaca tcatctgatc catgacttta tatttgaccc cttttttttg   5520

caaaagagag ggaaatactt aacgaaaatt tcctactgca ggagatcgat gccggaatta   5580

tctgggtgaa ctgctcgcaa ccctgcttct gccaagctcc atggggcggg aacaagcgca   5640

gcggctttgg acgcgagctc ggagaagggt gggtagcaca caacaatctc actttaaaac   5700

accatttcga tcgtctgatg atctcgacct gacatcatgc ctttggtatt ttcattcact   5760

tttcaggggc attgacaact acctaagcgt caagcaagtg acggagtacg cctccgatga   5820

gccgtgggga tggtacaaat ccccttccaa gctgtaa                            5857
```

<210> SEQ ID NO 2
<211> LENGTH: 1504
<212> TYPE: DNA
<213> ORGANISM: Oryza sativa

<400> SEQUENCE: 2

```
atggccacgg cgatcccgca gcggcagctc ttcgtcgccg gcgagtggcg cgcccccgcg     60

ctcggccgcc gcctccccgt cgtcaacccc gccaccgagt cccccatcgg cgagatcccg    120

gcgggcacgg cggaggacgt ggacgcggcg gtggcggcgg cgcgggaggc gcttaaaaag    180

aacccgggcc gcgactgggc gcccgcgccg ggcgccgtcc gggccaagta cattcgcgca    240

atcgctgaca aaataatcga gaggaaatct gagctggcta gactagagac gcttgattgt    300

gggaagcctc ttgatgaagc agcatgggac atggacgatg ttgctggatg ctttgagtac    360

tttgcagatc ttgcagaatc cttggacaaa aggcaaaatg cacctgtctc tcttccaatg    420

gaaaacttta aatgctatct tcggaaagag cctatcggtg tagttgggtt gatcacacct    480

tggaactatc ctctcctgat ggcaacatgg aaggtagctc ctgccctggc tgctggctgt    540

acagctgtac taaaaccatc tgaattggct tccgtgactt gtttggagct tgctgatgtg    600

tgtaaagagg ttggtcttcc ttcaggtgtg ctaaacatag tgactggatt aggttctgaa    660
```

-continued

```
gccggtgctc ctttgtcatc acaccctggt gtagacaagg ttgcatttac tgggagttat    720

gaaactggta tatatttcag ctgctcctat ggttaagcct gtttcactgg aacttggtgg    780

aaaaagtcct atagtggtgt ttgatgatgt tgatgttgaa aaagctgttg agtggactct    840

ctttggttgc ttttggacca atggccagat ttgcagtgca acatcgcgtc ttattcttca    900

taaaaaaatc gctaaagaat ttcaagaaag gatggttgca tgggccaaaa atattaaggt    960

gtcagatcca cttgaagagg gttgcaggct tgggcccgtt gttagtgaag gacagtatga   1020

gaagattaag caatttgtat ctaccgccaa aagccaaggt gctaccattc tgactggtgg   1080

ggttagaccc aagcatctgg agaaaggttt ctatattgaa cccacaatca ttactgatgt   1140

cgatacatca atgcaaattt ggagggaaga agtttttggt ccagtgctct gtgtgaaaga   1200

atttagcact gaagaagaag ccattgaatt ggccaacgat actcattatg gtctggctgg   1260

tgctgtgctt tccggtgacc gcgagcgatg ccagagatta actgaggaga tcgatgccgg   1320

aattatctgg gtgaactgct cgcaaccctg cttctgccaa gctccatggg gcgggaacaa   1380

gcgcagcggc tttggacgcg agctcggaga agggggcatt gacaactacc taagcgtcaa   1440

gcaagtgacg gagtacgcct ccgatgagcc gtggggatgg tacaaatccc cttccaagct   1500

gtaa                                                                1504


<210> SEQ ID NO 3
<211> LENGTH: 251
<212> TYPE: PRT
<213> ORGANISM: Oryza sativa

<400> SEQUENCE: 3

Met Ala Thr Ala Ile Pro Gln Arg Gln Leu Phe Val Ala Gly Glu Trp
 1               5                  10                  15

Arg Ala Pro Ala Leu Gly Arg Arg Leu Pro Val Val Asn Pro Ala Thr
            20                  25                  30

Glu Ser Pro Ile Gly Glu Ile Pro Ala Gly Thr Ala Glu Asp Val Asp
        35                  40                  45

Ala Ala Val Ala Ala Ala Arg Glu Ala Leu Lys Lys Asn Pro Gly Arg
    50                  55                  60

Asp Trp Ala Pro Ala Pro Gly Ala Val Arg Ala Lys Tyr Ile Arg Ala
65                  70                  75                  80

Ile Ala Asp Lys Ile Ile Glu Arg Lys Ser Glu Leu Ala Arg Leu Glu
                85                  90                  95

Thr Leu Asp Cys Gly Lys Pro Leu Asp Glu Ala Ala Trp Asp Met Asp
            100                 105                 110

Asp Val Ala Gly Cys Phe Glu Tyr Phe Ala Asp Leu Ala Glu Ser Leu
        115                 120                 125

Asp Lys Arg Gln Asn Ala Pro Val Ser Leu Pro Met Glu Asn Phe Lys
    130                 135                 140

Cys Tyr Leu Arg Lys Glu Pro Ile Gly Val Val Gly Leu Ile Thr Pro
145                 150                 155                 160

Trp Asn Tyr Pro Leu Leu Met Ala Thr Trp Lys Val Ala Pro Ala Leu
                165                 170                 175

Ala Ala Gly Cys Thr Ala Val Leu Lys Pro Ser Glu Leu Ala Ser Val
            180                 185                 190

Thr Cys Leu Glu Leu Ala Asp Val Cys Lys Glu Val Gly Leu Pro Ser
        195                 200                 205

Gly Val Leu Asn Ile Val Thr Gly Leu Gly Ser Glu Ala Gly Ala Pro
```

-continued

```
    210                 215                 220

Leu Ser Ser His Pro Gly Val Asp Lys Val Ala Phe Thr Gly Ser Tyr
225                 230                 235                 240

Glu Thr Gly Ile Tyr Phe Ser Cys Ser Tyr Gly
                245                 250


<210> SEQ ID NO 4
<211> LENGTH: 5859
<212> TYPE: DNA
<213> ORGANISM: Oryza sativa

<400> SEQUENCE: 4

atggccacgg cgatcccgca gcggcagctc ttcgtcgccg gcgagtggcg cgcccccgcg      60

ctcggccgcc gcctccccgt cgtcaacccc gccaccgagt cccccatcgg taccctcctc     120

ttcaccctct ccaccctctg cttctgcctc tgattagcct ttttgttgtt gttgttgttg     180

ctgctgtttt ttgcgtgtcg gtgcgcaggc gagatcccgg cgggcacggc ggaggacgtg     240

gacgcggcgg tggcggcggc gcgggaggcg ctgaagagga accggggccg cgactgggcg     300

cgcgcgccgg gcgccgtccg ggccaagtac ctccgcgcaa tcgcggccaa ggtagggtgg     360

tgactacccc cacccccccc cccccccaa cgcgacccgc gtgcgtgtgt tccgtacagg     420

gggaggagct ccgcgtggct ctccagtagg tttttgagcc ccaaatcgat cgatatgctc     480

tagttttaag tttgctgctt aaattcctca agggtttagt ttgcaaccaa atccttattt     540

tagcttcggt ataagccccc catatgatgt gcgtgcgtcg gcatcggaag tgcgtatcct     600

ctgttctgga ctaggaattg gccataggtt gatcgacagt tcgagtattc tgcttctgtt     660

tggaataagt tggaagcatg gctgattgtg tatctggatg ctgtttttgt ggtgattcgt     720

ttcaagctct tgttaattga tgggttcaag cggagagggt gcgcaacaac aagtgtatat     780

ggctcacggc catgggtgtg cacatttgat tggtgcgcaa caacaagtgt atattgtttg     840

tgtgcttcgt tagttggcag gtcctagtca ctaaatcact attggattgg tactagttac     900

ttttgtgcct tgacgatggg actggattac tagccttttg gttgcctttg tggtattccg     960

ttgttatggg cctgttgatg gatggatccc tttaatttct agtgccaaat gcatgctaga    1020

tttctcacag tttttctctt caggttatat ttctcgtatt tccttttcct aaaggattgc    1080

tttttcatgt attttctggc atatataggt tattattatt attattctcc agaacaagat    1140

tacccatatt atggatcact agtgtacact tttttggatg aaaaacctac ttactgaaag    1200

taaaacagtg accagtgcac actttacttg aactgtcaaa ccatcaattt tctagcaaag    1260

caggggatgc tagccttcca gtctaaatga cagtaaacta ctatactttt gtccgtaggt    1320

ttggaaatat gctaatttct atcataaaaa ttttcatggc atatgcgagc attttatgat    1380

caccttttcc ctttttcttc agataatcga gaggaaatct gagctggcta gactagagac    1440

gcttgattgt gggaagcctc ttgatgaagc agcatgggac atggtatgtg gccagttatc    1500

cactgtatga atatgtagtt gcctacacag caatctttcc tgaacatgaa tcctgatgta    1560

tgatattcca tttgtcagga cgatgttgct ggatgctttg agtactttgc agatcttgca    1620

gaatccttgg acaaaaggca aaatgcacct gtctctcttc caatggaaaa ctttaaatgc    1680

tatcttcgga aagagcctat cggtgtagtt gggttgatca caccttggta tttcacattt    1740

ttctctcatc ctgcgcttat atttatttat gacccaagca tggtactaaa tagtactagt    1800

aacatgcata tactgaatga gtttacaact ttacatgatt tttttgaact atgaaagttg    1860

aagacatttg agattttatt cctcttctct tgtgcaaaca tattattgtc tcacaaattg    1920
```

-continued

```
tacctagcag ctactctctc cgtttcatat tataagtcgt ttgacttttt tcctagtcaa   1980
aatgtgttaa gtttgaccaa gtttatagaa aaatttagca acatctaaaa tatcaaagtc   2040
atgttttagt gtttttttcag gctctcatgt aagcaatttt gatgtgccct ctcctttctt   2100
cttaatataa tgatacacag ctcttgtgta ttcaaaggaa aatatatata tatataatga   2160
tacacacctc tcctccgtgt taatgcagct catttgttct gtcccggttc aaatatctat   2220
ttttctcata tgttgtcagc atgattcact taatttagta tatagaagat gccattattt   2280
atgtctggaa tcttactgca gaagggaaaa caattgataa cggaattgat tgcattctaa   2340
tttgttgttt ctttgttatg ttcttatcga caattacaaa tttgattctg agaatcatgt   2400
tcgggatgtg tatttctact gcaggaacta tcctctcctg atggcaacat ggaaggtagc   2460
tcctgccctg gctgctggct gtacagctgt actaaaacca tctgaattgg cttccgtgta   2520
agtttaacat gttaacttgt taatgtcata cccatgctag ttgcaatgac atttgatttt   2580
aaaatgttgt ggcatgtcca tgctgcaagc aatgtaattt gaaatctctc tctatcatta   2640
attaccagga cttgtttgga gcttgctgat gtgtgtaaag aggttggtct tccttcaggt   2700
gtgctaaaca tagtgactgg attaggttct gaagccggtg ctcctttgtc atcacaccct   2760
ggtgtagaca aggtacagct attcctcctg taatcatgta taccccatca atggaaatga   2820
tattcctctc aatacatggt ttatgttttc tgttaggttg catttactgg gagttatgaa   2880
actggtaaaa agattatggc ttcagctgct cctatggtta aggtttgttt ccaaatttct   2940
gtggatattt tttgttctct ttctactaac tctctattat caattctcaa tgttgtcctt   3000
ttcttttaac tcctttactt tttagaattg tgatcaagac actttgagca tcattctagt   3060
agccagttct atcctgtttc ttaccttttt atggttcgtc ttttcttgac agcctgtttc   3120
actggaactt ggtggaaaaa gtcctatagt ggtgtttgat gatgttgatg ttgaaaaagg   3180
tacatgccac ttgctatgat taactaattc tgaagtgcgg gactttgtaa agcacttaac   3240
tgagctggat gctagacccc caaaagccct ttttggtgtc ttgggcttgt tgcagaaata   3300
ctggtcccag acgagcagga tgcaagaaaa ttaactactt ttgccactga ttagtatttc   3360
ttagaagtta cacctcaagg attagcaata ctttcttaaa atgtgctatt gattaaaaag   3420
atgtcctgta ttattttgag cagatcttgt actggttgat cggcttgcat gaaaatattg   3480
ttgaggatta taatgccatg ccaactgagt aaagaaaaga gttgtaaaat atgttatgca   3540
acatgaatat atatgtgatt tcatttttcc tttttctttt cgtggcaagg aaggcagtta   3600
ggaaggactg atgtgaaaag cacaagtact attcttagtt ctggaaaact gtgttcttta   3660
ttttcctaac tacaattcac cttgattagt cagtaacttg atattggcaa ttctagctga   3720
ttatgaattc tgtttatatt tcactaattt tgaatcttta attacatttt atggttgaaa   3780
tttaacgttt tgtctggtta tggactctgt ttgtattcac tcaatttgga tcttccatta   3840
gatttcattg ttggtccttc ttcttgtaca gctgttgagt ggactctctt tggttgcttt   3900
tggaccaatg gccagatttg cagtgcaaca tcgcgtctta ttcttcatgt aagcattgaa   3960
tatatccgtc aatcataatc tattgttgta cttgattttt tttctgatca actcctgagt   4020
tcagattatt atatgatgcc attactattg cacagagcga ataaaattgt atttatgcac   4080
agcatgtatt ttgagtaata tatgcattgc ctattattta atatatagat tgtagcactt   4140
aattttgtgt ccatgtctct atgatgttta ttactttatt attgccggca tgaagcaact   4200
ttgaactcta tgttgatctt gaactaaaat tgaaattaat tggcttattg ctattaatga   4260
```

-continued

```
tatagctttc agcttcttgc tcctgaccat gaaagttttg cagaaaaaaa tcgctaaaga   4320
atttcaagaa aggatggttg catgggccaa aaatattaag gtgtcagatc cacttgaaga   4380
gggttgcagg cttgggcccg ttgttagtga aggacaggta ccacatgtaa actttttcta   4440
aattcaaaaa agaaatgcca ctgatcaatg gtaggtcctt ccaagcctta ttgctggatt   4500
gttgcactgt tttgtcaatt ttgtgtaata tagttctgaa tgaattagtc ggtgtatgct   4560
cttgctagtt gctagtatgt ggtacagggt cttcctactt tgagcaaatt cgtgttaaaa   4620
tgcattgatg aaaaggccac ctttccgtag gtttatcttg tcataattta aaccccaata   4680
aaattttaat tttttgtttt gaccccatgg cactttaatg aaatcactta gccatgagct   4740
tttgtatata ttttcaaagc accagaatgt ttagatggtt tgttggaaat cttacacatc   4800
ctattgcctt gtgtcagtat gagaagatta agcaatttgt atctaccgcc aaaagccaag   4860
gtgctaccat tctgactggt ggggttagac ccaaggtaat aatctactac acggttgtat   4920
atataggtac ccacatatca ttatgaagta gaaataatct tgtatgtttt tgtcagcatc   4980
tggagaaagg tttctatatt gaacccacaa tcattactga tgtcgataca tcaatgcaaa   5040
tttggaggga agaagttttt ggtccagtgc tctgtgtgaa agaatttagc actgaagaag   5100
aagccattga attggccaac gatactcagt gagttttttt tttaatacag ttcattgtcc   5160
tgttcaatct tgcagcatat gtatatactc tgtggcatat gaacttattc tgctactact   5220
acttttgata gttatggtct ggctggtgct gtgctttccg gtgaccgcga gcgatgccag   5280
agattaactg aggtatatcc aagtgaaggg ggttggcatt gtttgattca tatgacatgg   5340
ttgcatcaag ctgatattca agaatctcat ttattacttg cattctatgc atctccagtt   5400
cttccctgga ctccggtcaa tgttaatata gtttgtttgc tagtagtatg ctactccaat   5460
taagttgctc ttcacttcca catcatctga tccatgactt tatatttgac cccttttttt   5520
tgcaaaagaa agggaaatac ttaacgaaaa tttcctactg caggagatcg atgccggaat   5580
tatctgggtg aactgctcgc aaccctgctt ctgccaagct ccatggggcg ggaacaagcg   5640
cagcggcttt ggacgcgagc tcggagaagg gtgggtagca cacaacaatc tcactttaaa   5700
acaccatttc gatcgtctga tgatctcgac ctgacatcat gcctttggta ttttcattca   5760
cttttcaggg gcattgacaa ctacctaagc gtcaagcaag tgacggagta cgcctccgat   5820
gagccgtggg gatggtacaa atccccttcc aagctgtaa                          5859
```

<210> SEQ ID NO 5
<211> LENGTH: 1512
<212> TYPE: DNA
<213> ORGANISM: Oryza sativa

<400> SEQUENCE: 5

```
atggccacgg cgatcccgca gcggcagctc ttcgtcgccg gcgagtggcg cgcccccgcg     60
ctcggccgcc gcctccccgt cgtcaacccc gccaccgagt cccccatcgg cgagatcccg    120
gcgggcacgg cggaggacgt ggacgcggcg gtggcggcgg cgcgggaggc gctgaagagg    180
aaccggggcc gcgactgggc gcgcgcgccg ggcgccgtcc gggccaagta cctccgcgca    240
atcgcggcca agataatcga gaggaaatct gagctggcta gactagagac gcttgattgt    300
gggaagcctc ttgatgaagc agcatgggac atggacgatg ttgctggatg ctttgagtac    360
tttgcagatc ttgcagaatc cttggacaaa aggcaaaatg cacctgtctc tcttccaatg    420
gaaaacttta aatgctatct tcggaaagag cctatcggtg tagttgggtt gatcacacct    480
tggaactatc ctctcctgat ggcaacatgg aaggtagctc ctgccctggc tgctggctgt    540
```

-continued

```
acagctgtac taaaaccatc tgaattggct tccgtgactt gtttggagct tgctgatgtg    600

tgtaaagagg ttggtcttcc ttcaggtgtg ctaaacatag tgactggatt aggttctgaa    660

gccggtgctc ctttgtcatc acaccctggt gtagacaagg ttgcatttac tgggagttat    720

gaaactggta aaaagattat ggcttcagct gctcctatgg ttaagcctgt ttcactggaa    780

cttggtggaa aaagtcctat agtggtgttt gatgatgttg atgttgaaaa agctgttgag    840

tggactctct ttggttgctt ttggaccaat ggccagattt gcagtgcaac atcgcgtctt    900

attcttcata aaaaaatcgc taaagaattt caagaaagga tggttgcatg ggccaaaaat    960

attaaggtgt cagatccact tgaagagggt tgcaggcttg ggcccgttgt tagtgaagga   1020

cagtatgaga agattaagca atttgtatct accgccaaaa gccaaggtgc taccattctg   1080

actggtgggg ttagacccaa gcatctggag aaaggtttct atattgaacc cacaatcatt   1140

actgatgtcg atacatcaat gcaaatttgg agggaagaag tttttggtcc agtgctctgt   1200

gtgaaagaat ttagcactga agaagaagcc attgaattgg ccaacgatac tcattatggt   1260

ctggctggtg ctgtgctttc cggtgaccgc gagcgatgcc agagattaac tgaggagatc   1320

gatgccggaa ttatctgggt gaactgctcg caaccctgct tctgccaagc tccatggggc   1380

gggaacaagc gcagcggctt tggacgcgag ctcggagaag gggcattga caactaccta   1440

agcgtcaagc aagtgacgga gtacgcctcc gatgagccgt ggggatggta caaatcccct   1500

tccaagctgt aa                                                       1512
```

<210> SEQ ID NO 6
<211> LENGTH: 503
<212> TYPE: PRT
<213> ORGANISM: Oryza sativa

<400> SEQUENCE: 6

```
Met Ala Thr Ala Ile Pro Gln Arg Gln Leu Phe Val Ala Gly Glu Trp
 1               5                  10                  15

Arg Ala Pro Ala Leu Gly Arg Arg Leu Pro Val Val Asn Pro Ala Thr
            20                  25                  30

Glu Ser Pro Ile Gly Glu Ile Pro Ala Gly Thr Ala Glu Asp Val Asp
        35                  40                  45

Ala Ala Val Ala Ala Ala Arg Glu Ala Leu Lys Arg Asn Arg Gly Arg
    50                  55                  60

Asp Trp Ala Arg Ala Pro Gly Ala Val Arg Ala Lys Tyr Leu Arg Ala
65                  70                  75                  80

Ile Ala Ala Lys Ile Ile Glu Arg Lys Ser Glu Leu Ala Arg Leu Glu
                85                  90                  95

Thr Leu Asp Cys Gly Lys Pro Leu Asp Glu Ala Ala Trp Asp Met Asp
            100                 105                 110

Asp Val Ala Gly Cys Phe Glu Tyr Phe Ala Asp Leu Ala Glu Ser Leu
        115                 120                 125

Asp Lys Arg Gln Asn Ala Pro Val Ser Leu Pro Met Glu Asn Phe Lys
    130                 135                 140

Cys Tyr Leu Arg Lys Glu Pro Ile Gly Val Val Gly Leu Ile Thr Pro
145                 150                 155                 160

Trp Asn Tyr Pro Leu Leu Met Ala Thr Trp Lys Val Ala Pro Ala Leu
                165                 170                 175

Ala Ala Gly Cys Thr Ala Val Leu Lys Pro Ser Glu Leu Ala Ser Val
            180                 185                 190
```

-continued

```
Thr Cys Leu Glu Leu Ala Asp Val Cys Lys Glu Val Gly Leu Pro Ser
        195                 200                 205

Gly Val Leu Asn Ile Val Thr Gly Leu Gly Ser Glu Ala Gly Ala Pro
    210                 215                 220

Leu Ser Ser His Pro Gly Val Asp Lys Val Ala Phe Thr Gly Ser Tyr
225                 230                 235                 240

Glu Thr Gly Lys Lys Ile Met Ala Ser Ala Ala Pro Met Val Lys Pro
                245                 250                 255

Val Ser Leu Glu Leu Gly Gly Lys Ser Pro Ile Val Val Phe Asp Asp
            260                 265                 270

Val Asp Val Glu Lys Ala Val Glu Trp Thr Leu Phe Gly Cys Phe Trp
        275                 280                 285

Thr Asn Gly Gln Ile Cys Ser Ala Thr Ser Arg Leu Ile Leu His Lys
    290                 295                 300

Lys Ile Ala Lys Glu Phe Gln Glu Arg Met Val Ala Trp Ala Lys Asn
305                 310                 315                 320

Ile Lys Val Ser Asp Pro Leu Glu Glu Gly Cys Arg Leu Gly Pro Val
                325                 330                 335

Val Ser Glu Gly Gln Tyr Glu Lys Ile Lys Gln Phe Val Ser Thr Ala
            340                 345                 350

Lys Ser Gln Gly Ala Thr Ile Leu Thr Gly Gly Val Arg Pro Lys His
        355                 360                 365

Leu Glu Lys Gly Phe Tyr Ile Glu Pro Thr Ile Ile Thr Asp Val Asp
    370                 375                 380

Thr Ser Met Gln Ile Trp Arg Glu Glu Val Phe Gly Pro Val Leu Cys
385                 390                 395                 400

Val Lys Glu Phe Ser Thr Glu Glu Glu Ala Ile Glu Leu Ala Asn Asp
                405                 410                 415

Thr His Tyr Gly Leu Ala Gly Ala Val Leu Ser Gly Asp Arg Glu Arg
            420                 425                 430

Cys Gln Arg Leu Thr Glu Glu Ile Asp Ala Gly Ile Ile Trp Val Asn
        435                 440                 445

Cys Ser Gln Pro Cys Phe Cys Gln Ala Pro Trp Gly Gly Asn Lys Arg
    450                 455                 460

Ser Gly Phe Gly Arg Glu Leu Gly Glu Gly Gly Ile Asp Asn Tyr Leu
465                 470                 475                 480

Ser Val Lys Gln Val Thr Glu Tyr Ala Ser Asp Glu Pro Trp Gly Trp
                485                 490                 495

Tyr Lys Ser Pro Ser Lys Leu
            500
```

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gccatgccaa ctgagtaaag 20

<210> SEQ ID NO 8
<211> LENGTH: 20
<212> TYPE: DNA
<213> ORGANISM: Artificial Sequence
<220> FEATURE:
<223> OTHER INFORMATION: Primer -continued

<400> SEQUENCE: 8
caattttatt cgctctgtgc 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgcaacatcg cgtcttattc 20

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gcaactagca agagcataca cc 22

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
acctgacatc atgcctttgg 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ccggtcatca gctaacttcc 20

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
cccttcgtca taaaatatac tagcaa 26

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tcctccaaca tgctctttcg 20

<210> SEQ ID NO 15

-continued

<211> LENGTH: 20
<212> TYPE: DNA
<213> ORGANISM: Artificial Sequence
<220> FEATURE:
<223> OTHER INFORMATION: Primer

<400> SEQUENCE: 15
cagagaagtt tacgccgttg 20

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
tttttaaata agatgaacgg tcaaa 25

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ctctccaccc tctgcttctg 20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ctctccgctt gaacccatc 19

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gcatggctga ttgtgtatct g 21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ttccaaacct acggacaaaa g 21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21

-continued ttcctcttct cttgtgcaaa c 21

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cacggaagcc aattcagatg 20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
ctatcctctc ctgatggcaa c 21

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
tggctactag aatgatgctc aaag 24

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ccttttgtgt cgcttttgag 20

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
aaaatagcct tcactcgttg c 21

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccatcgattt cgagggtaac 20

<210> SEQ ID NO 28
<211> LENGTH: 19
<212> TYPE: DNA

-continued

<213> ORGANISM: Artificial Sequence
<220> FEATURE:
<223> OTHER INFORMATION: Primer

<400> SEQUENCE: 28
cgcatccgat aatatgttg 19

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
gtaattagga gtacgactct cgtc 24

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gcttatagcc tactgtatcc tcctc 25

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
aattggttaa cccagcaagc 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
acattgtgaa acggaggaag 20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gctataagcc agctgcaaac 20

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
gcagttggta cggacttcg 19

-continued

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
cctaaatatt tgacgccgtt g 21

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tgaagaggag ggtaccgatg 20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
caccactcca cacctgacac 20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gtacggaaca cacgcacaag 20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
tgttgttgtt gttgctgctg 20

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
gccgtgagcc atatacactt g 21

<210> SEQ ID NO 41
<211> LENGTH: 20
<212> TYPE: DNA
<213> ORGANISM: Artificial Sequence
<220> FEATURE:

-continued

<223> OTHER INFORMATION: Primer

<400> SEQUENCE: 41
agctccagct cctcctcgat 20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
tatctctcac cgaccccaaa 20

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
tgttgccatc aggagagga 19

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ctcttgatga agcagcatgg 20

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
cccagtaaat gcaaccttgt c 21

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
ggcaacatgg aaggtagctc 20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ccatgcaacc atcctttctt 20

-continued

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ttatggcttc agctgctcct 20

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
caatggcttc ttcttcagtg c 21

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gcccgttgtt agtgaaggac 20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
gtaccatccc cacggctcat 20

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52
cgagcgatgc cagagatta 19

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
agcacatggc aaatcaaaca 20

<210> SEQ ID NO 54
<211> LENGTH: 20
<212> TYPE: DNA
<213> ORGANISM: Artificial Sequence
<220> FEATURE:
<223> OTHER INFORMATION: Primer -continued

<400> SEQUENCE: 54
tgctcctttg tcatcacacc 20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
tttccaccaa gttccagtga 20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ttcgctgcag aacagatgac 20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
ctgatggtta cgcgacaatt t 21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
atttgaaccg ggacagaaca 20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
ttttgatgtg ccctctcctt 20

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
tgggtaatct tgttctggag 20

<210> SEQ ID NO 61
<211> LENGTH: 20

-continued

<212> TYPE: DNA
<213> ORGANISM: Artificial Sequence
<220> FEATURE:
<223> OTHER INFORMATION: Primer

<400> SEQUENCE: 61
agtgccaaat gcatgctaga 20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
tggggctcaa aaacctactg 20

<210> SEQ ID NO 63
<211> LENGTH: 18
<212> TYPE: DNA
<213> ORGANISM: Artificial Sequence
<220> FEATURE:
<223> OTHER INFORMATION: Primer

<400> SEQUENCE: 63
gtccgggcca agtacctc 18

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
atctctcacc gaccccaaat 20

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
ccattggaag agagacaggt g 21

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
tgttgttgtt gttgctgctg 20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67

-continued tggggctcaa aaacctactg 20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
ggttggtctt ccttcaggtg 20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ggtccaaaag caaccaaaga 20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
actggtaaaa agattatggc 20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
caagccgatc aaccagtaca 20

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
ccatgctgca agcaatgta 19

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
aaccatagga gcagctgaaa ta 22

<210> SEQ ID NO 74
<211> LENGTH: 20
<212> TYPE: DNA
<213> ORGANISM: Artificial Sequence -continued
<220> FEATURE:
<223> OTHER INFORMATION: Primer

<400> SEQUENCE: 74
accctggtgt agacaaggta 20

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
gggagttatg aaactggtat at 22

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
ataggagcag ctgaagccat 20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
gtcccgcact tcagaattag 20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
ctctgcttct gcctctgatt 20

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
ctggctacta gaatgatgct c 21

<210> SEQ ID NO 80
<211> LENGTH: 30
<212> TYPE: DNA
<213> ORGANISM: Artificial Sequence
<220> FEATURE:
<223> OTHER INFORMATION: Primer

<400> SEQUENCE: 80
aattccatgg ggttggtctt ccttcaggtg 30

-continued

<210> SEQ ID NO 81
<211> LENGTH: 30
<212> TYPE: DNA
<213> ORGANISM: Artificial Sequence
<220> FEATURE:
<223> OTHER INFORMATION: Primer

<400> SEQUENCE: 81
aattactagt ttccaccaag ttccagtgaa 30

<210> SEQ ID NO 82
<211> LENGTH: 30
<212> TYPE: DNA
<213> ORGANISM: Artificial Sequence
<220> FEATURE:
<223> OTHER INFORMATION: Primer

<400> SEQUENCE: 82
aattgctagc ggtccaaaag caaccaaaga 30

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
cttgttgaat tagatggtga tgtt 24

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
gttgtgggag ttgtagttgt attc 24

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
tagcttcaca tccccatgtg 20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
gcaccttcac atcttgctgt 20

<210> SEQ ID NO 87
<211> LENGTH: 20
<212> TYPE: DNA
<213> ORGANISM: Artificial Sequence
<220> FEATURE:
<223> OTHER INFORMATION: Primer -continued

<400> SEQUENCE: 87
acatcgccct ggactatgac 20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
tgctgagaga tgccaagatg 20

<210> SEQ ID NO 89
<211> LENGTH: 56
<212> TYPE: DNA
<213> ORGANISM: Oryza rufipogon

<400> SEQUENCE: 89
tgcatttact gggagttatg aaactggtat atatttcagc tgctcctatg gttaag 56

<210> SEQ ID NO 90
<211> LENGTH: 56
<212> TYPE: DNA
<213> ORGANISM: Oryza rufipogon

<400> SEQUENCE: 90
tgcatttact gggagttatg aaactggtat atatttcagc tgctcctatg gttaag 56

<210> SEQ ID NO 91
<211> LENGTH: 56
<212> TYPE: DNA
<213> ORGANISM: Oryza rufipogon

<400> SEQUENCE: 91
tgcatttact gggagttatg aaactggtat atatttcagc tgctcctatg gttaag 56

<210> SEQ ID NO 92
<211> LENGTH: 64
<212> TYPE: DNA
<213> ORGANISM: Oryza rufipogon

<400> SEQUENCE: 92
tgcatttact gggagttatg aaactggtaa aaagattatg gcttcagctg ctcctatggt 60
taag 64

<210> SEQ ID NO 93
<211> LENGTH: 56
<212> TYPE: DNA
<213> ORGANISM: Oryza nivara

<400> SEQUENCE: 93
tgcatttact gggagttatg aaactggtat atatttcagc tgctcctatg gttaag 56

<210> SEQ ID NO 94
<211> LENGTH: 64
<212> TYPE: DNA
<213> ORGANISM: Oryza nivara

<400> SEQUENCE: 94
tgcatttact gggagttatg aaactggtaa aaagattatg gcttcagctg ctcctatggt 60

-continued

```
taag                                                                64


<210> SEQ ID NO 95
<211> LENGTH: 64
<212> TYPE: DNA
<213> ORGANISM: Oryza sativa

<400> SEQUENCE: 95

tgcatttact gggagttatg aaactggtaa aaagattatg gcttcagctg ctcctatggt     60

taag                                                                64


<210> SEQ ID NO 96
<211> LENGTH: 10
<212> TYPE: PRT
<213> ORGANISM: Oryza sativa

<400> SEQUENCE: 96

Val Thr Leu Glu Leu Gly Gly Lys Ser Pro
 1               5                  10
```